(12) United States Patent
Caprioli et al.

(10) Patent No.: US 10,607,721 B2
(45) Date of Patent: Mar. 31, 2020

(54) HIGH-THROUGHPUT, MULTI-OMICS APPROACH TO DETERMINE AND VALIDATE DE NOVO GLOBAL MECHANISMS OF ACTION FOR DRUGS AND TOXINS

(71) Applicant: Vanderbilt University, Nashville, TN (US)

(72) Inventors: Richard Caprioli, Nashville, TN (US); John Wikswo, Nashville, TN (US); John McLean, Nashville, TN (US); Eric Skaar, Nashville, TN (US); Jeremy L. Norris, Nashville, TN (US); Dana Borden Lacy, Nashville, TN (US); Stacy Sherrod, Nashville, TN (US); James Pino, Nashville, TN (US); Danielle Gutierrez, Nashville, TN (US); Nicole D. Muszynski, Nashville, TN (US); Melissa Farrow, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 347 days.

(21) Appl. No.: 15/273,259

(22) Filed: Sep. 22, 2016

(65) Prior Publication Data
US 2017/0082606 A1 Mar. 23, 2017

Related U.S. Application Data

(60) Provisional application No. 62/221,657, filed on Sep. 22, 2015.

(51) Int. Cl.
*G16B 40/00* (2019.01)
*G01N 33/50* (2006.01)
*G01N 33/573* (2006.01)

(52) U.S. Cl.
CPC ......... *G16B 40/00* (2019.02); *G01N 33/5008* (2013.01); *G01N 33/573* (2013.01); *G01N 2500/20* (2013.01)

(58) Field of Classification Search
CPC .................................................. G16B 40/00
USPC ........................................................ 702/19
See application file for complete search history.

(56) References Cited

U.S. PATENT DOCUMENTS 5,376,355 A * 12/1994 Turteltaub ......... A61K 51/0423
424/1.11
2013/0035257 A1 * 2/2013 Yu .......................... C12N 11/04
506/11

OTHER PUBLICATIONS

Ahuja, V., and Sharma, S. "Drug safety testing paradigm, current progress and future challenges: an overview." *J Appl Toxicol* 34, 576-594, 2014.
Di Bernardo et al., "Chemogenomic profiling on a genome-wide scale using reverse-engineered gene networks." *Nat. Biotechnol.*, 23 (3), 377-383, 2005.
Engelberg, A. "Iconix Pharmaceuticals, Inc.—removing barriers to efficient drug discovery through chemogenomics." *Pharmacogenomics* 5, 741-744, 2004.
Kalgutkar, A.S., and Soglia, J.R., "Minimising the potential for metabolic activation in drug discovery." *Expert Opin Drug Metab Toxicol* 1, 91-142, 2005.
Kalgutkar et al., A comprehensive listing of bioactivation pathways of organic functional groups. *Curr Drug Metab* 6, 161-225, 2005.
Krejsa et al., "Predicting ADME properties and side effects: the BioPrint approach." *Curr Opin Drug Discov Devel* 6, 470-480, 2003.
Milne et al., "Sum of the parts: mass spectrometry-based metabolomics." *Biochemistry* 52, 3829-3840, 2013.
Sasseville et al., "Testing paradigm for prediction of development-limiting barriers and human drug toxicity." *Chem Biol Interact* 150, 9-25, 2004.
Wikswo, J.P., "The relevance and potential roles of microphysiological systems in biology and medicine." *Exp. Biol. Med.*, 239 (9), 1061-1072, 2014.
Woo et al., "Elucidating Compound Mechanism of Action by Network Perturbation Analysis." *Cell*, 162 (2), 441-451, 2015.

* cited by examiner

*Primary Examiner* — Jerry Lin
(74) *Attorney, Agent, or Firm* — Parker Highlander PLLC

(57) ABSTRACT

The present disclosure provides for rapid identification of mechanism of action (MOA) for drugs and toxins, and does so in a rapid (30 days or less) fashion. The methods use a combination of high throughput bioinformatics and pathway analysis that examine a wide variety of biological parametics.

11 Claims, 11 Drawing Sheets
(11 of 11 Drawing Sheet(s) Filed in Color)

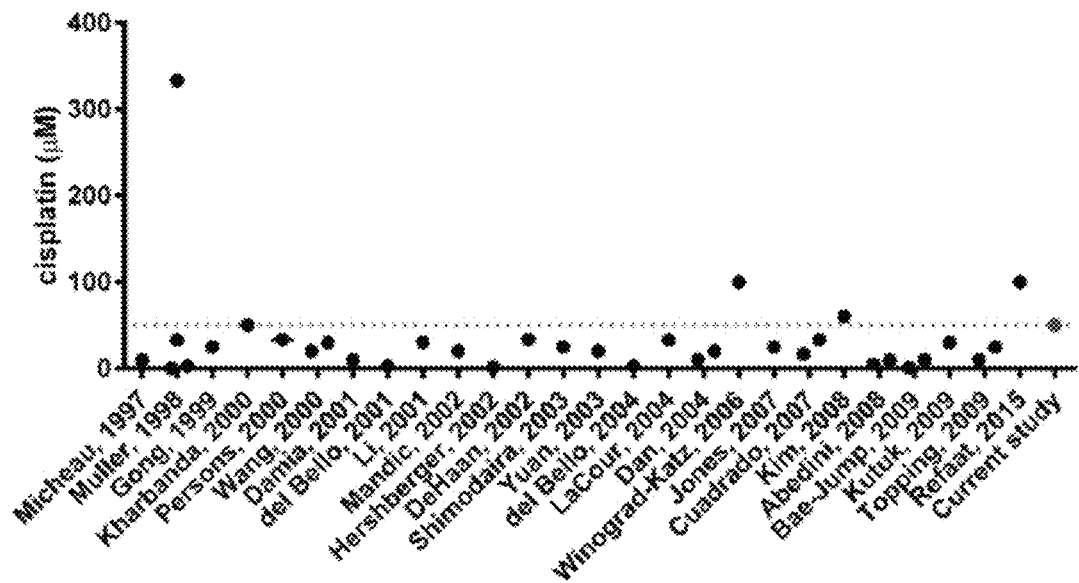
FIG. 8
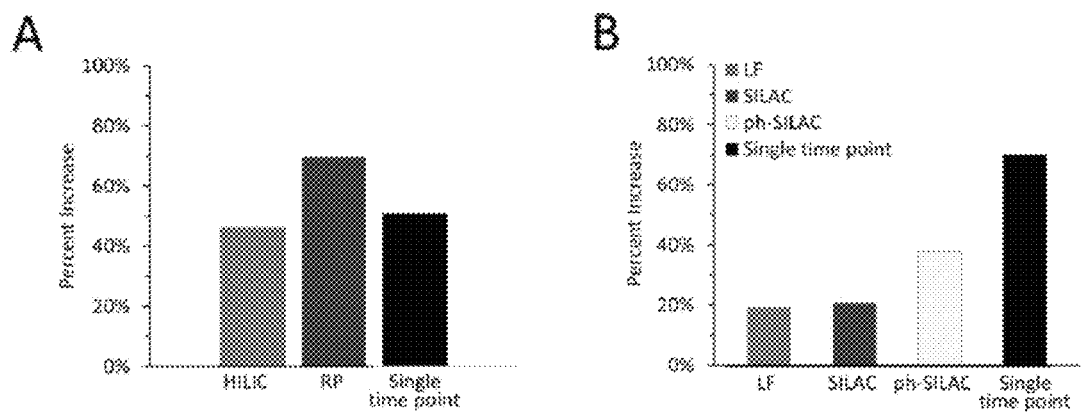
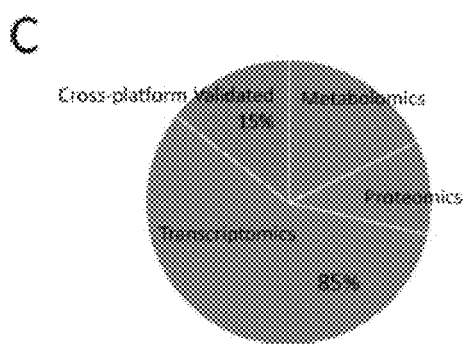
FIGS. 9A-C

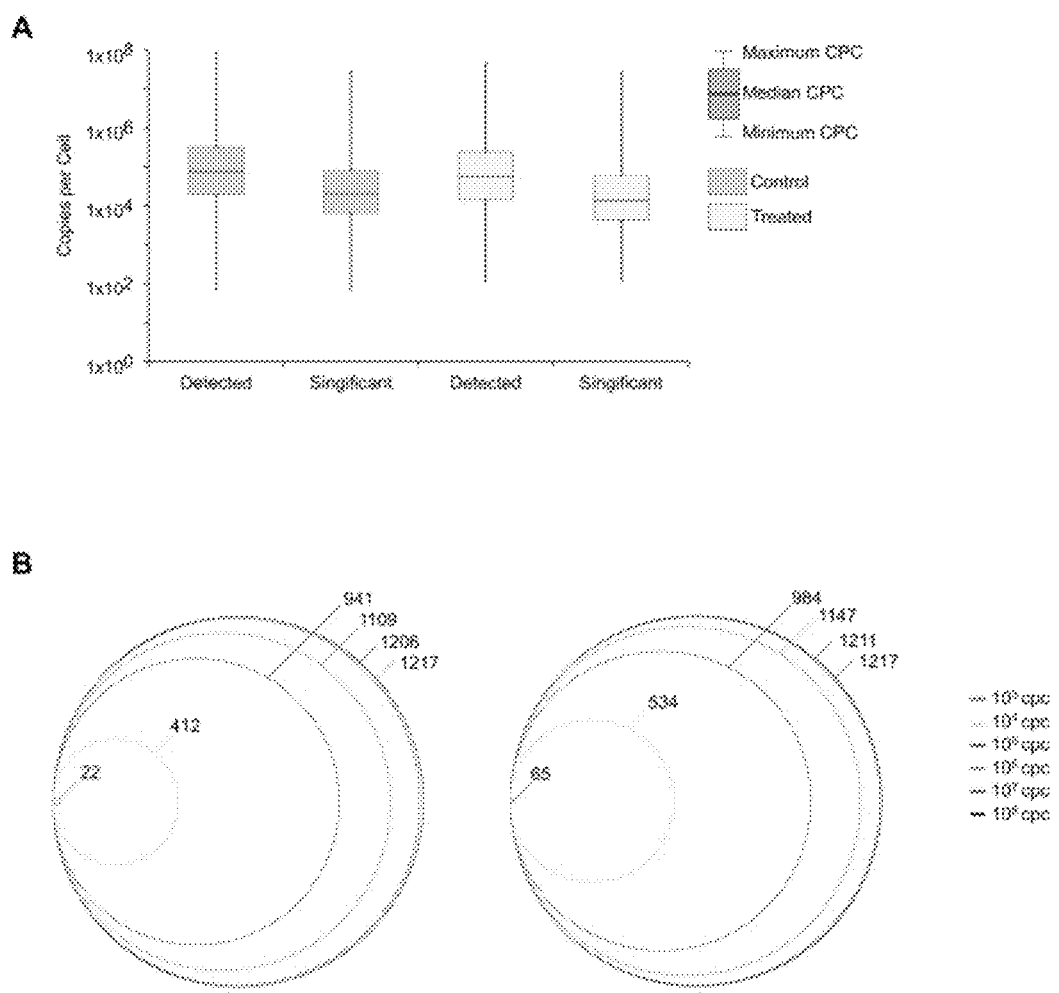
FIGS. 10A-B

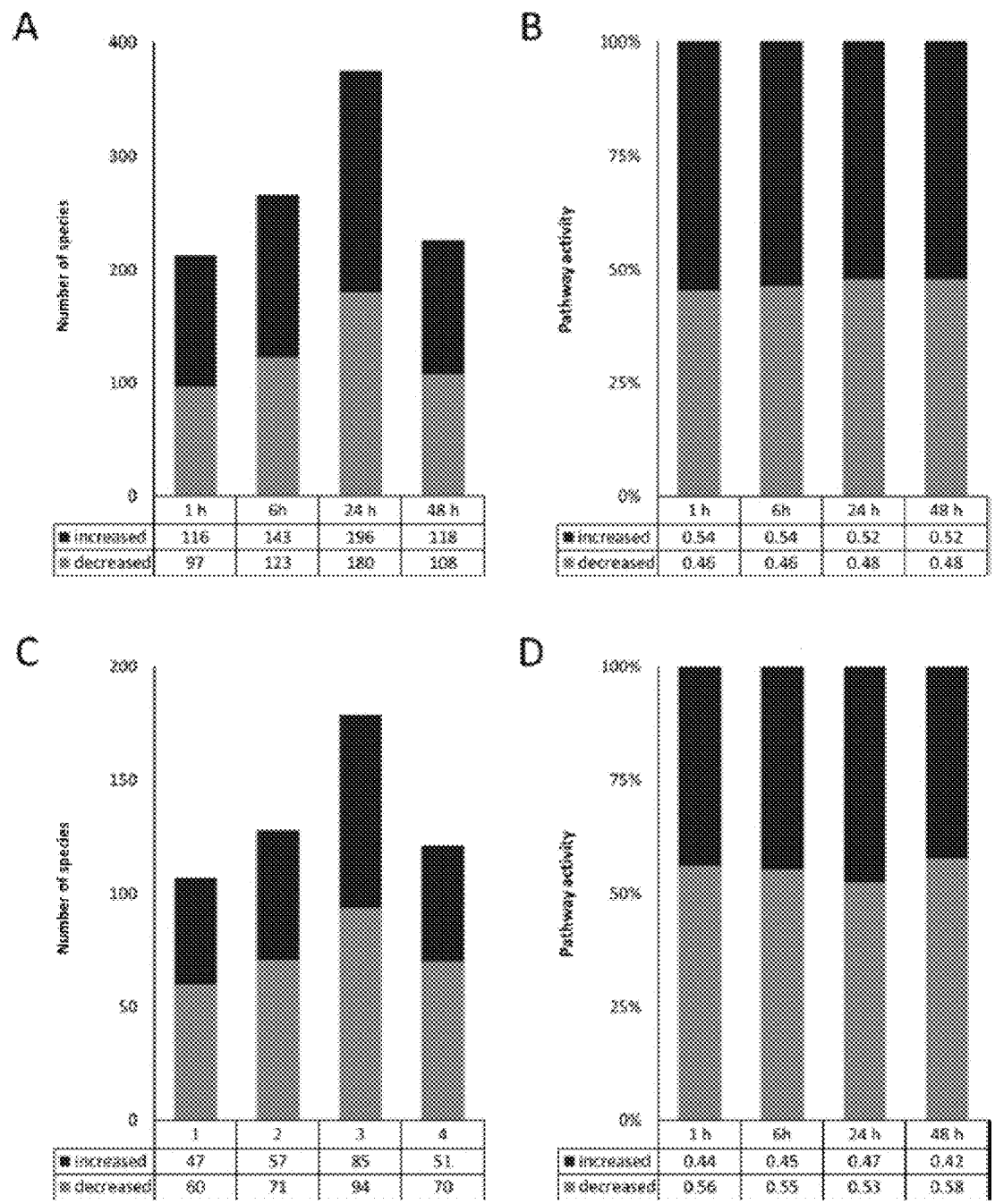
FIGS. 13A-D

HIGH-THROUGHPUT, MULTI-OMICS APPROACH TO DETERMINE AND VALIDATE DE NOVO GLOBAL MECHANISMS OF ACTION FOR DRUGS AND TOXINS

BACKGROUND

This application claims benefit of priority to U.S. Provisional Application Ser. No. 62/221,657, filed Sep. 22, 2015, the entire contents of which are hereby incorporated by reference.

This invention was made with government support under Cooperative Agreement Number W911 NF-14-2-0022 awarded by the U.S. Army Research Office and the Defense Advanced Research Projects Agency. The government has certain rights in the invention.

1. FIELD

The disclosure relates to the fields of molecular and cellular biology, cell physiology, and pharmacology. More particularly, the disclosure relates to rapid methods for the identification of molecular mechanism of drug action.

2. DESCRIPTION OF RELATED ART

Under the current paradigm for drug development, it costs approximately $2.6 billion and approximately 12 years to develop and introduce a drug to the market, representing an increase of 145% between 2003 and 2013 (Crawford, 2010; Tufts Center for the Study of Drug Development, 2014). One of the documented factors contributing to this increased cost is the decline in R&D efficiency for the development of new drugs (Paul et al., 2010; Pammoli et al., 2011; Scannell et al., 2012). Historically, drug development has focused on the optimization of drug efficacy toward a single target, assuming that maximizing affinity toward that target will result in the best clinical endpoint. Toward this end, pre-clinical research has been optimized, automated and systematized in recent years to generate drug candidates at increasingly efficient rates. In spite of the increase in pre-clinical efficiency, failure rate of drug candidates in clinical trial has remained unchanged. Recent estimates suggest that approximately only one in five to ten developed drug candidates will succeed (DiMasi et al., 2010; Hay et al., 2014; Kola and Landis, 2004). The factors leading to failure of drug candidates in a trial are numerous, and include lack of efficacy and safety concerns, effects on the patient population that are difficult to predict with targeted assays (Hay et al., 2014; Kola and Landis, 2004). Drug binding is promiscuous leading to off-target effects and ultimately impacting overall efficacy. In contrast to recent history, R&D efficiency in drug development was more effective when animals (e.g., systems) were used in the initial screen rather than automated molecular assays. These findings now suggests this reductionist approach to drug development may be flawed and that the criterion used for the selection of drug candidates for clinical trial may be insufficient to select for compounds that maximize the rate of success since the inventors should be simultaneously optimizing for multiple attributes of the molecules, not only affinity to a single target.

Current approaches to drug development rely on targeted medium to high-throughput approaches, such as reverse phase protein array (RPMA), protein-fragment complementation assay (PCA), and high content screening (HCT), which measure hundreds to thousands proteins pre-selected based on knowledge of known biology. Similarly, current pre-clinical safety testing evaluates absorption, distribution, metabolism, and excretion and the potential for toxicity using pre-selected endpoints of specific tests (in silico analyses, genotoxicity tests, organ system tests, and in vivo analyses) to determine if a compound will continue development (Ahuja and Sharma, 2014). Current toxicology screens can efficiently determine the potential for toxicity and adverse reactions due to the structural and physiochemical properties of the compound and can use known toxicity profiles to evaluate potential toxicity of a candidate drug due to secondary mechanisms of action (Ahuja and Sharma, 2014; Engelberg, 2004; Kalgutkar et al., 2005; Kalgutkar and Soglia, 2005; Krejsa et al., 2003; Sasseville et al., 2004). However, current technologies fall short of defining the full MOA of a candidate drug at the early stages of development and can only identify problems within the mechanisms that are being probed (Ahuja and Sharma, 2014). Better understanding a compound's MOA during pre-clinical development could improve prediction of its potential for success.

SUMMARY

Thus, in accordance with the present disclosure, there is provided a method of identifying a biological mechanism for a drug or toxin comprising:
(a) providing a known or unknown drug or toxin;
(b) determining an optimal dosage and exposure time for said drug or toxin on a biological system, wherein said optimal dosage and exposure time maximizes the observation of one or more biological parameters of a biological mechanism in said biological system;
(c) exposing said drug or toxin under said optimal dosage and exposure time to said biological system;
(d) assessing one or more of said biological parameters in said biological system that is/are altered, as compared to an untreated biological system, thereby identifying one or more biological effects for said drug or toxin; and
(e) applying a bioinformatic analysis to the one or more biological effects of step (d) to identify one or more biological mechanisms for said drug or toxin.

The biological system may be a purified enzyme, a purified subcellular organelle, a cell, a tissue, an organ, an organ system or an organism.

Determining an optimal dosage and exposure time may comprise exposing said biological system to a plurality of different doses and exposure time, and measuring one or more effects of said drug or toxin on said biological system. The one or more effects may comprises change enzyme activity, protein levels, nucleic acid levels, lipid levels, carbohydrate levels, metabolite levels, protein phosphorylation levels, post translational modification, average protein size, organelle function, tissue integrity or function, organ function, cell morphology, integrity, activity or viability, or organism activity or viability, such as cell viability determined by microscopy or by a biological marker (e.g., caspase activation or ATP utilization).

Step (d) may comprise RPLC, HILIC chromatography, RNA sequencing, mass spectrometry, ion mobility mass spectrometry, genomic analysis, protein array, or immunoassay. Steps (c) and (d) may be performed for multiple time points. Step (b) may comprises (i) first determining an optimal dosage and exposure time for said drug or toxin on cell viability; and then (ii) determining an optimal dosage and exposure time for said drug or toxin on changes in protein, RNA or metabolite levels in a comparable cell. Step (b)(ii) may comprise RPLC, HILIC chromatography, RNA sequencing, mass spectrometry, ion mobility mass spectrometry, genomic analysis, protein array, or immunoassay.

The method may further comprising validating said one or more biological parameters, such as by mechanistic validation and/or cross-platform validation. The bioinformatics analysis may comprise applying a canonical mechanism analysis and/or an empirical mechanism analysis to the one or more biological effects in step (e). Steps (a)-(e) may be performed in 30 days or less.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

(FIG. 2A) Two stages of the screening are illustrated. The phenotypic screens evaluate physiological changes to narrow the exposure to a small number of responsive conditions. The molecular screen focuses these possibilities to the optimal conditions. The green boxes represent theoretical dose ranges. (FIG. 2B) This cartoon conceptualizes the inventors' approach to determine optimal exposure conditions. The green box highlights the ideal target dose range, one that stimulates the greatest molecular response while maintaining a tolerable level of cell viability. (FIGS. 2C and 2D) Phenotypic screening results for cisplatin at 24 h show (FIG. 2C) relative caspase activation (ApoONE) and (FIG. 2D) cell viability (CellTiter Glo). The green boxes demonstrate effective responses. (FIG. 2E) Qualitative evaluation of the cell viability at 24 h confirms an optimal dose range. Green: live cells; red: dead cells. (FIG. 2F) MALDI FTICR MS spectra from a 6 h exposure illustrate molecular differences in control (top, black) and 50 μM cisplatin-treated samples (bottom, green). The inset highlights differences in the molecular signatures of the control and treated samples within a selected m/z region (see asterisks). (FIG. 2G) This graph summarizes the results of the molecular screen. The green box indicates the selected dose for Phase 2 discovery experiments.

(FIG. 3A) Significantly changed proteins (based on gene symbol) and (FIG. 3B) identified (top) and significantly changed (bottom) metabolites show the overlap across the modalities and time. For visual simplicity, 3 out of 4 time points are shown. Abbreviations: LF—label-free; HILIC—hydrophilic liquid interaction chromatography; RP—reverse phase chromatography. (FIG. 3C) Transcriptomic data show the overlap of significantly changed transcripts across time. (FIG. 3D) A cross-platform comparison of unique, significantly changed species shows the overlap between transcriptomics and proteomics.

(FIG. 4A) The cisplatin canonical MOA generated from a literature survey (green). (FIG. 4B) A vignette of the intrinsic apoptosis pathway illustrates directional-fold changes and detection status from the empirical data. Abbreviations: ERK: ERK1/2; ERKP: ERK1 pThr202/pTyr204 and ERK2 pThr185/pTyr187; p53P: p53 pSer392. (FIG. 4C) This workflow conceptualizes the reconstruction of networks from seeding species. (FIG. 4D) An overlay of the ECN (green) and the DDN (blue) demonstrates the comprehensive nature of empirical mechanism construction beyond the canonical mechanism.

(FIG. 5A) The CUL4B/HUWE1 pathway (pink) can modulate the intrinsic apoptosis pathway (green). (FIG. 5B) Relative caspase activation (top) and % viability (ATP levels; bottom) of 50 μM cisplatin-treated cells compared to untreated. (FIG. 5C) Superimposition of the ERN (red) and the DDN (blue) demonstrates capture of known and potentially novel resistance mechanisms. (FIG. 5D) ATP1A1 regulates Ncx1 activity (orange), which can affect the regulation of apoptosis. (FIG. 5E) This pathway illustrates the estrogen-induced cisplatin resistance mechanism (teal). (FIG. 5F) The STIP1 cascade (purple) initiates STIP-1 and PRNP interaction and endocytosis, which ultimately leads to phosphorylation of BAD and inhibition of apoptosis.

FIG. 8. Cisplatin dose (related to FIGS. 2A-G). The dose selected through the inventors' screening process aligns well with typical cisplatin doses when compared to literature used to generate the canonical cisplatin mechanism of action FIGS. 9A-C. Data increase through use of multiple modalities (related to FIGS. 3A-D). (FIG. 9A) This graph demonstrates the metabolomics coverage observed using a combined hydrophobic/hydrophilic chromatography approach. Both hydrophilic interaction liquid chromatography (HILIC) and reversed-phase chromatography (RPLC) generated a similar number of identified features by IM-MS analysis, approximately 6,000 for HILIC and 8,000 for RPLC analysis, but less than half of these molecules are observed across both LC methods (see FIGS. 3A-D). The additional coverage afforded by combining HILIC and RPLC analysis allowed for 46% (gray bar) and 70% (blue bar) more identifications than using either technique alone, illustrating the importance of using multiple separation techniques based on disparate chemical affinities to detect a greater diversity of species and improve the identification and quantification of significantly changed species. Furthermore, 51% of the total number of statistically significant metabolite species identified (tentative structural identifications, see methods) were not represented in more than a single time point (black bar). The large number of unique metabolites observed at 24 h (see FIGS. 3A-D) suggests that as exposure time of cisplatin increases, the metabolism of the cell is altered. It is important to note that the global metabolomics data shown represent only those species identified through database correlation and statistically prioritized based on the significance criteria of the study (see metabolomics methods). (FIG. 9B) The inventors' proteomic approach utilized three modalities: label-free analysis (LF), SILAC of unenriched samples, and SILAC of samples enriched for phosphorylation (ph-SILAC). All proteomic modalities were complementary, with 78% of the significantly changed proteins unique to any one modality (LF: 19%, dark gray bar; SILAC: 21%, blue bar; ph-SILAC: 38%, light gray bar). The majority of significantly changed phosphorylated proteins quantified via ph-SILAC were not determined as significantly changed, either as modified or unmodified, by the other two modalities. These results underscore the value of using multiple proteomic technologies to assess perturbations due to exogenous compound exposure, and parallelization can provide rapid and extensive coverage of the altered proteome. Furthermore, 70% of the significantly changed proteins were unique to a single time point, either 1, 6, or 24 h (black bar). (FIG. 9C) Unique, significant changes from each platform were compared by gene symbol. The various technology modalities each contributed greatly to this dataset, with 85% unique to a single technology (blue sections: metabolomics: 18%; proteomics: 11%; transcriptomics: 57%). Overall, 1,963 species were cross-validated (gray section). This represents 15% of the total unique, significantly changed species. The combined, synergistic nature of multi-omics data has advantages for throughput, depth and breadth of molecular coverage, temporal understanding, and fidelity. Each platform, taken independently, permits only limited sensitivity and dynamic range. A multi-omics approach provides for validation of molecular changes across multiple platforms. Serial validation performed after initial discovery experiments using orthogonal techniques, such as Western blotting, has the advantages of detecting targeted compounds and activation events; however, it is expensive, labor intensive, and is limited in scale and throughput. For situations where the utmost stringency is desired, a MOA can be constructed only from cross-validated species. In this current proof-of-concept application, the number of cross-validated species quantified for an empirical cisplatin MOA far outweighs the number of proteins determined in the literature as a canonical mechanism.

FIGS. 10A-B. Estimated sensitivity of SILAC analysis (related to FIG. 3A). (FIG. 10A) Copies per cell for detected and significantly changed proteins were estimated using the method described in O'Grady et al. (2014) from the SILAC datasets. (FIG. 10B) The left and right panels show the number of significantly changed proteins found at or below the specified copies per cell range in control and treated samples, respectively. The color of the circles indicates protein concentration (copies per cell) for the quantified proteins. For MS signal, the inventors used protein intensities from the MaxQuant protein group report, which were calculated by summing the intensities of unmodified peptides and oxidized Met-containing peptides per protein group, including unique and razor peptides. For DNA mass, the inventors used the value estimated by O'Grady et al. (2014) for diploid human cells, 6.5 pg/cell. While the A549 cell line available through the American Type Culture Collection is not diploid, O'Grady et al. (2014) showed similar estimates for total protein per cell measured by three different methods: the proteomic ruler, cell counting and protein concentration, and expected (6.5 pg/cell) to actual DNA content multiplied by total sample protein. To determine histone MS signal, all datasets were combined and the intensities of all histones (including modified forms) were summed.

FIGS. 13A-D. IPA analysis of species and pathway activity (related to FIGS. 5A and B). (FIG. 13A) The total number of species at each time point associated with an increase (dark blue) or decrease (light blue) in apoptosis are shown. (FIG. 13B) The species shown in panel A were normalized to the total number of species at each time point and are shown as a percentage representing the overall increase or decrease in apoptotic activity. (FIG. 13C) The total number of species at each time point associated with an increase (dark blue) or decrease (light blue) in viability are shown. (FIG. 13D) The species shown in FIG. 13C were normalized to the total number of species at each time point and are shown as a percentage representing the overall increase or decrease in viability.

DESCRIPTION OF ILLUSTRATIVE EMBODIMENTS

Figure 1:
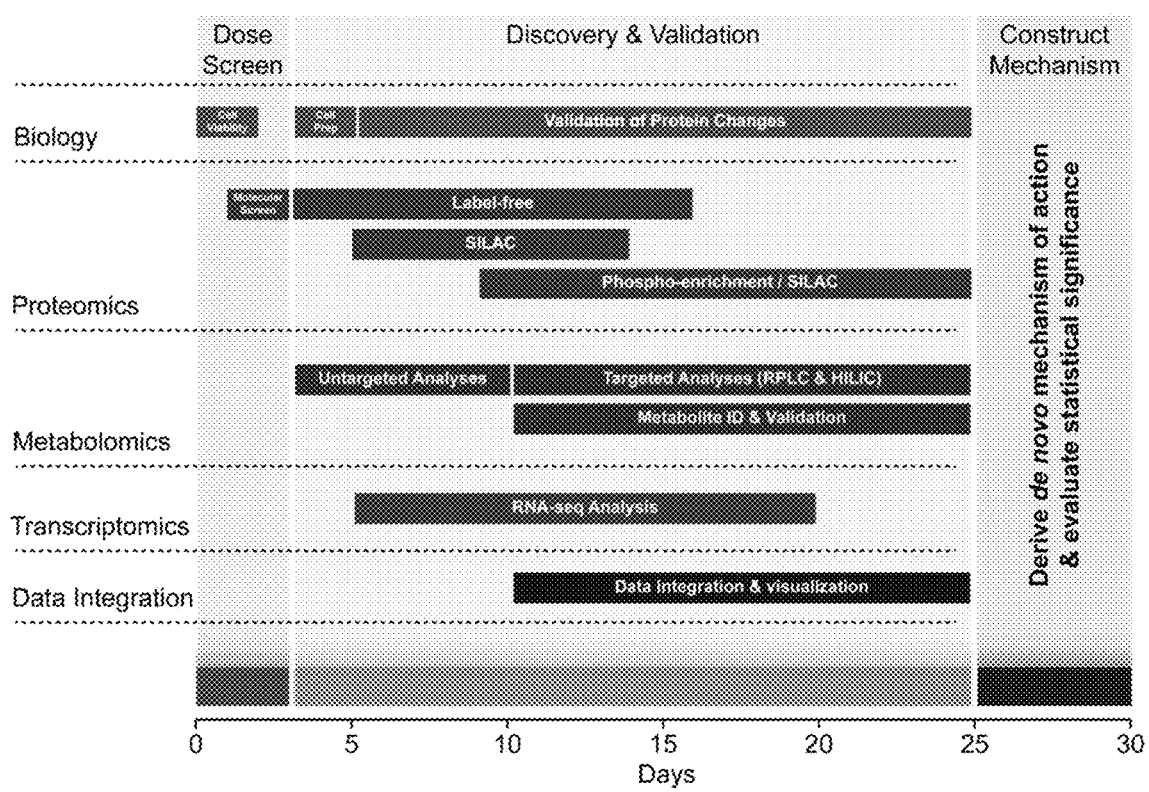
FIG. 1. Multi-omics platform for MOA construction. The 30-day procedure has three distinct phases: dose screen (days 0-3), discovery and validation (days 4-25), and mechanism construction (days 26-30). Phase 1 incorporates cell viability and molecular screens to establish protocols for the discovery phase. Phase 2 integrates proteomics, metabolomics, and transcriptomics to determine molecular changes correlated with compound exposure. In Phase 3, network analysis of all statistically significant changes drives construction of a comprehensive MOA.

The cellular response to most of the drugs and common toxicants to which humans are ubiquitously exposed has not been comprehensively characterized on a molecular basis. The discovery and evaluation of the mechanism of action (MOA) of unknown exogenous compounds has historically been a time consuming, expensive, and difficult process; therefore, it is rarely undertaken. Nevertheless, there remains an urgent need to develop global, high-throughput, effective strategies to assess mechanisms of action for exogenous compounds on human cells. Access to technologies that can provide a comprehensive view of MOA will fundamentally change the way the inventors evaluate potential therapeutic drugs and toxins that pose a threat to human health. In order to diminish the challenges of drug development and more quickly respond to chemical threats it is essential to develop a strategy to quickly and efficiently evaluate MOA on a global scale and through which affected cellular processes can be identified. Recent advances in multi-omics technologies used for transcriptomics, proteomics, and metabolomics now provide unprecedented speed while maintaining a high standard for data quality. The prevailing dogma regarding these technologies is that they are not applicable in situations that require high throughput results (Sereni et al., 2013). This increase in analytical efficiency, coupled with modern computational capabilities to organize and assist in interpreting the vast amount of data generated by these technologies, now makes it feasible to obtain comprehensive data to confirm MOA for a compound. Further, this approach also provides an opportunity to better characterize biological processes that are impacted by the compound that are unexpected.

Here, the investigators describe an integrated multi-omics approach that can empirically derive a global MOA for a compound in a high-throughput manner—30 days or less. Next-generation sequencing technologies provide the deepest coverage in a high-throughput cost effective manner Transciptome analysis can identify tens of thousands of changes due to cellular perturbation; however, it does not give a complete understanding of the cellular state or a compound's MOA. This is due to post-translational modifications expanding the proteome beyond a 1:1 ratio of transcript:protein and due to the formation of protein complexes, both of which can alter the activity and/or the function of a protein (Sereni et al., 2013). There are over 200 known post-translational modifications (Jensen, 2004; Walsh, 2006) and it is estimated that the 20,000-25,000 human genes (International Human Genome Sequencing, 2004) yield over 100,000 mRNA transcripts which produce over 1 million different proteins (Jensen, 2004; Walsh, 2006; Walsh et al., 2005). Mass spectrometry-based proteomics is the gold standard for determining the type and location of specific post-translational modifications to proteins. In addition to transcriptomics and proteomics, metabolomics plays an integral role in obtaining a global view of a compound's MOA. Profiling the metabolic state of cells after perturbation provides insight into signaling mechanisms and cellular energetics and can reveal metabolic phenotypes associated with disease states (Milne et al., 2013).

By combining each of these approaches, as well as others, the investigators have developed a comprehensive approach to drug/toxin MOA analysis. Here, the inventors describe an integrated analytical and computational approach that empirically derives a global MOA for a compound in less than 30 days. They demonstrated proof-of-principle for this technology platform using cisplatin, a well-established DNA damage-inducing chemotherapeutic. Research over the past 20 years establishes a few dozen compounds implicated in cisplatin's primary MOA. In 30 days, this platform quantified over 10,000 unique molecular changes, including 55% of the species in an expanded canonical network Importantly, the data captured novel pathways that may inform clinical observations of cisplatin resistance. A driving aim for this technology is to move beyond the limits of targeted analyses informed by established pathways and to provide a technology for the accelerated understanding of MOA. These and other aspets of the disclosure are discussed below.

I. DETECTION—MASS SPECTROMETY

By exploiting the intrinsic properties of mass and charge, mass spectrometry (MS) can resolved and confidently identified a wide variety of complex compounds, including proteins, nucleic acids, lipids and other metabolites. Traditional quantitative MS has used electrospray ionization (ESI) followed by tandem MS (MS/MS) (Chen et al., 2001; Thong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000).

1. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

2. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI- TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

3. SIMS

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

4. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectrum.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

5. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

6. Ion-Mobility Spectrometry

Ion-mobility spectrometry (IMS) is an analytical technique used to separate and identify ionized molecules in the gas phase based on their mobility in a carrier buffer gas. Though heavily employed for military or security purposes, such as detecting drugs and explosives, the technique also has many laboratory analytical applications, recently being coupled with mass spectrometry and high-performance liquid chromatography. IMS devices come in a wide range of sizes (often tailored for a specific application) and are capable of operating under a broad range of conditions. Systems operated at higher pressure (i.e., atmospheric conditions, 1 atm or 1013 mbar) are also accompanied by elevated temperature (above 100° C.), while lower pressure systems (1-20 mbar) do not require heating.

Ion-mobility spectrometry-mass spectrometry (IMS-MS), also known as ion-mobility separation-mass spectrometry, is an analytical chemistry method that separates gas phase ions on a millisecond timescale using ion-mobility spectrometry and uses mass spectrometry on a microsecond timescale to identify components in a sample. The IM-MS technique can be used for analyzing complex mixtures based on differing mobilities in an electric field. The gas-phase ion structure can be studied using IM-MS through measurement of the CCS and comparison with CCS of standard samples or CCS calculated from molecular modelling. The signal-to-noise ratio is obviously improved because the noise can be physically separated with signal in IM-MS. In addition, isomers can be separated if their shapes are different. The peak capacity of IM-MS is much larger than MS so more compounds can be found and analyzed. This character is very critical for-omics study which requires analyzing as many compounds as possible in a single run. It has been used in the detection of chemical warfare agents, detection of explosives, in proteomics for the analysis of proteins, peptides, drug-like molecules and nanoparticles.

II. NUCLEIC ACID DETECTION VIA HYBRIDIZATION AND AMPLIFICATION

In alternative embodiments for detecting protein expression, one may assay for gene transcription. For example, an indirect method for detecting protein expression is to detect mRNA transcripts from which the proteins are made. The following is a discussion of such methods.

1. Hybridization

There are a variety of ways by which one can assess gene expression. These methods either look at protein or at mRNA levels. Methods looking at mRNAs all fundamentally rely, at a basic level, on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present disclosure in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present disclosure are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Since many mRNAs are present in relatively low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously (Chamberlan et al., 1990). The presence of many PCR primers in a single tube could cause many problems, such as the increased formation of misprimed PCR products and "primer dimers", the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255 and Mueller and Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present disclosure are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present disclosure. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present disclosure (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present disclosure.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present disclosure, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present disclosure.

Other methods of nucleic acid detection that may be used in the practice of the instant disclosure are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

5. Next Generation Signaling

Next-generation sequencing applies to genome sequencing, genome resequencing, transcriptome profiling (RNA-Seq), DNA-protein interactions (ChIP-sequencing), and epigenome characterization. Resequencing is necessary, because the genome of a single individual of a species will not indicate all of the genome variations among other individuals of the same species.

The high demand for low-cost sequencing has driven the development of high-throughput sequencing (or next-generation sequencing) technologies that parallelize the sequencing process, producing thousands or millions of sequences concurrently. High-throughput sequencing technologies are intended to lower the cost of DNA sequencing beyond what is possible with standard dye-terminator methods. In ultra-high-throughput sequencing as many as 500,000 sequencing-by-synthesis operations may be run in parallel.

Massively Parallel Signature Sequencing (MPSS).

The first of the next-generation sequencing technologies, massively parallel signature sequencing (or MPSS), was developed in the 1990s at Lynx Therapeutics, a company founded in 1992 by Sydney Brenner and Sam Eletr. MPSS was a bead-based method that used a complex approach of adapter ligation followed by adapter decoding, reading the sequence in increments of four nucleotides. This method made it susceptible to sequence-specific bias or loss of specific sequences. Because the technology was so complex, MPSS was only performed 'in-house' by Lynx Therapeutics and no DNA sequencing machines were sold to independent laboratories. Lynx Therapeutics merged with Solexa (later acquired by Illumina) in 2004, leading to the development of sequencing-by-synthesis, a simpler approach acquired from Manteia Predictive Medicine, which rendered MPSS obsolete. However, the essential properties of the MPSS output were typical of later "next-generation" data types, including hundreds of thousands of short DNA sequences. In the case of MPSS, these were typically used for sequencing cDNA for measurements of gene expression levels.

Polony Sequencing.

The Polony sequencing method, developed in the laboratory of George M. Church at Harvard, was among the first next-generation sequencing systems and was used to sequence a full *E. coli* genome in 2005. It combined an in vitro paired-tag library with emulsion PCR, an automated microscope, and ligation-based sequencing chemistry to sequence an *E. coli* genome at an accuracy of >99.9999% and a cost approximately 1/9 that of Sanger sequencing.

454 Pyrosequencing.

A parallelized version of pyrosequencing was developed by 454 Life Sciences, which has since been acquired by Roche Diagnostics. The method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence readouts. This technology provides intermediate read length and price per base compared to Sanger sequencing on one end and Solexa and SOLiD on the other.

Illumina (Solexa) Sequencing.

Solexa, now part of Illumina, was founded by Shankar Balasubramanian and David Klenerman in 1998, and developed a sequencing method based on reversible dye-terminators technology, and engineered polymerases. The terminated chemistry was developed internally at Solexa and the concept of the Solexa system was invented by Balasubramanian and Klenerman from Cambridge University's chemistry department. In 2004, Solexa acquired the company Manteia Predictive Medicine in order to gain a massively parallel sequencing technology invented in 1997 by Pascal Mayer and Laurent Farinelli. It is based on "DNA Clusters" or "DNA colonies," which involves the clonal amplification of DNA on a surface.

In this method, DNA molecules and primers are first attached on a slide or flow cell and amplified with polymerase so that local clonal DNA colonies, later coined "DNA clusters," are formed. To determine the sequence, four types of reversible terminator bases (RT-bases) are added and non-incorporated nucleotides are washed away. A camera takes images of the fluorescently-labeled nucleotides. Then the dye, along with the terminal 3' blocker, is chemically removed from the DNA, allowing for the next cycle to begin. Unlike pyrosequencing, the DNA chains are extended one nucleotide at a time and image acquisition can be performed at a delayed moment, allowing for very large arrays of DNA colonies to be captured by sequential images taken from a single camera.

Decoupling the enzymatic reaction and the image capture allows for optimal throughput and theoretically unlimited sequencing capacity. With an optimal configuration, the ultimately reachable instrument throughput is thus dictated solely by the analog-to-digital conversion rate of the camera, multiplied by the number of cameras and divided by the number of pixels per DNA colony required for visualizing them optimally (approximately 10 pixels/colony). In 2012, with cameras operating at more than 10 MHz A/D conversion rates and available optics, fluidics and enzymatics, throughput can be multiples of 1 million nucleotides/second, corresponding roughly to 1 human genome equivalent at 1× coverage per hour per instrument, and 1 human genome re-sequenced (at approx. 30×) per day per instrument (equipped with a single camera).

SOLiD Sequencing.

Applied Biosystems' (now a Life Technologies brand) SOLiD technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Illumina sequencing. This sequencing by ligation method has been reported to have some issue sequencing palindromic sequences.

Ion Torrent Semiconductor Sequencing.

Ion Torrent Systems Inc. (now owned by Life Technologies) developed a system based on using standard sequencing chemistry, but with a novel, semiconductor based detection system. This method of sequencing is based on the detection of hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

DNA Nanoball Sequencing.

DNA nanoball sequencing is a type of high throughput sequencing technology used to determine the entire genomic sequence of an organism. The company Complete Genomics uses this technology to sequence samples submitted by independent researchers. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run and at low reagent costs compared to other next generation sequencing platforms. However, only short sequences of DNA are determined from each DNA nanoball which makes mapping the short reads to a reference genome difficult. This technology has been used for multiple genome sequencing projects and is scheduled to be used for more.

Helicos Single Molecule Fluorescent Sequencing.

Heliscope sequencing is a method of single-molecule sequencing developed by Helicos Biosciences. It uses DNA fragments with added poly-A tail adapters which are attached to the flow cell surface. The next steps involve extension-based sequencing with cyclic washes of the flow cell with fluorescently labeled nucleotides (one nucleotide type at a time, as with the Sanger method). The reads are performed by the Heliscope sequencer. The reads are short, averaging 35 bp. In 2009 a human genome was sequenced using the Heliscope, however in 2012 the company went bankrupt.

Single Molecule Real Time Sequencing.

SMRT sequencing is based on the sequencing by synthesis approach. The DNA is synthesized in zero-mode waveguides (ZMWs)—small well-like containers with the capturing tools located at the bottom of the well. The sequencing is performed with use of unmodified polymerase (attached to the ZMW bottom) and fluorescently labelled nucleotides flowing freely in the solution. The wells are constructed in a way that only the fluorescence occurring by the bottom of the well is detected. The fluorescent label is detached from the nucleotide upon its incorporation into the DNA strand, leaving an unmodified DNA strand. According to Pacific Biosciences (PacBio), the SMRT technology developer, this methodology allows detection of nucleotide modifications (such as cytosine methylation). This happens through the observation of polymerase kinetics. This approach allows reads of 20,000 nucleotides or more, with average read lengths of 5 kilobases.

III. IMMUNOASSAYS

Thus, in accordance with the present disclosure, methods are provided for the assaying proteins using immunologic methods, i.e., with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (See, e.g., Antibodies: A Laboratory Manual, Cold Spring Harbor Laboratory, 1988; incorporated herein by reference).

In accordance with the present disclosure, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle & Ben-Zeev O, 1999; Gulbis & Galand, 1993; De Jager et al., 1993; and Nakamura et al., 1987, each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the disclosure. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present disclosure is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

Type II Assay.

In Type II assay formats, a limited amount of antibody is used (insufficient to bind the entire antigen) a prefixed amount of labeled antigen competes with the unlabeled antigen in test sample for a limited number of antibody binding sites. The concentration of unlabeled antigen in specimen can be determined from the portion of labeled antigen that is bound to the antibody. Since most analyte molecules are not enough large to provide two different epitopes in this method, the response will be inversely proportional to the concentration of antigen in the unknown.

Homogenous and Heterogenous Assay.

The use off either competitive or immunometric assays requires differentition of bound from free label. This can be archived either by seperating bound from free label using a means of removing antibody (heterogeeous) or modulation of signal of the label when antigen is bound to antibody cpmapred to when it is free (homogeneous).

Most solid phase immunoassays belong to the Heterogeneous Assay category. There are many ways of seperating bound from free label such as precipitation of antibody, chromatographic method, and solid pahse coupling antibody. Homogeneous assays do not require any of separation step to distinguish antigen bound antibody from free antibody. It has an advantage in automation, and typically is faster, easier to perform, and more cost-effective, but its specificty and sensitivity are lower.

Immunochromatography.

There is two different immunochromatography assays based on porous materials—nitrocellulose or nylon membrane. Depending on the liquid migration method, these are classified as lateral flow assay (LFA) or flow through assay (FTA). LFA methods are described in U.S. Pat. No. 6,485, 982 is original patent belong to IMA.

2D-Gel Electrophoresis.

2-D electrophoresis begins with 1-D electrophoresis but then separates the molecules by a second property in a direction 90 degrees from the first. In 1-D electrophoresis, proteins (or other molecules) are separated in one dimension, so that all the proteins/molecules will lie along a lane but that the molecules are spread out across a 2-D gel. Because it is unlikely that two molecules will be similar in two distinct properties, so molecules are more effectively separated in 2-D electrophoresis than in 1-D electrophoresis.

The two dimensions that proteins are separated into using this technique can be isoelectric point, protein complex mass in the native state, and protein mass. To separate the proteins by isoelectric point is called isoelectric focusing (IEF). Thereby, a gradient of pH is applied to a gel and an electric potential is applied across the gel, making one end more positive than the other. At all pHs other than their isoelectric point, proteins will be charged. If they are positively charged, they will be pulled towards the more negative end of the gel and if they are negatively charged they will be pulled to the more positive end of the gel. The proteins applied in the first dimension will move along the gel and will accumulate at their isoelectric point; that is, the point at which the overall charge on the protein is 0 (a neutral charge).

A typical second dimensional separation is SDS-PAGE. Before separating the proteins by mass, they are treated with sodium dodecyl sulfate (SDS) along with other reagents (SDS-PAGE in 1-D). This denatures the proteins (that is, it unfolds them into long, straight molecules) and binds a number of SDS molecules roughly proportional to the protein's length. Because a protein's length (when unfolded) is roughly proportional to its mass, this is equivalent to saying that it attaches a number of SDS molecules roughly proportional to the protein's mass. Since the SDS molecules are negatively charged, the result of this is that all of the proteins will have approximately the same mass-to-charge ratio as each other. In addition, proteins will not migrate when they have no charge (a result of the isoelectric focusing step) therefore the coating of the protein in SDS (negatively charged) allows migration of the proteins in the second dimension (NB SDS is not compatible for use in the first dimension as it is charged and a nonionic or zwitterionic detergent needs to be used). In the second dimension, an electric potential is again applied, but at a 90 degree angle from the first field. The proteins will be attracted to the more positive side of the gel proportionally to their mass-to-charge ratio. As previously explained, this ratio will be nearly the same for all proteins. The proteins' progress will be slowed by frictional forces. The gel therefore acts like a molecular sieve when the current is applied, separating the proteins on the basis of their molecular weight with larger proteins being retained higher in the gel and smaller proteins being able to pass through the sieve and reach lower regions of the gel.

Proteins can then be detected by a variety of means, but the most commonly used stains are silver and Coomassie Brilliant Blue staining. In this case, a silver colloid is applied to the gel. The silver binds to cysteine groups within the protein. The silver is darkened by exposure to ultra-violet light. The darkness of the silver can be related to the amount of silver and therefore the amount of protein at a given location on the gel. This measurement can only give approximate amounts, but is adequate for most purposes.

C. Dipstick Technology

U.S. Pat. No. 4,366,241, and Zuk, EP-A 0 143 574 describe migration type assays in which a membrane is impregnated with the reagents needed to perform the assay. An analyte detection zone is provided in which labeled analyte is bound and assay indicia is read.

U.S. Pat. No. 4,770,853, WO 88/08534, and EP-A 0 299 428 describe migration assay devices which incorporate within them reagents which have been attached to colored direct labels, thereby permitting visible detection of the assay results without addition of further substances.

U.S. Pat. No. 4,632,901, disclose a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

EP-A 0 125 118, disclose a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

EP-A 0 282 192, disclose a dipstick device for use in competition type assays.

U.S. Pat. No. 4,313,734 describes the use of gold sol particles as a direct label in a dipstick device.

U.S. Pat. No. 4,786,589 describes a dipstick immunoassay device in which the antibodies have been labeled with formazan.

U.S. Pat. No. 5,656,448 pertains to dipstick immunoassay devices comprising a base member and a single, combined sample contact zone and test zone, wherein the test zone incorporates the use of symbols to detect analytes in a sample of biological fluid. A first immunological component, an anti-immunoglobulin capable of binding to an enzyme-labeled antibody, is immobilized in a control indicator portion. A second immunological component, capable of specifically binding to a target analyte which is bound to the enzyme-labeled antibody to form a sandwich complex, is immobilized in a test indicia portion. The enzyme-labeled antibody produces a visual color differential between a control indicia portion and a non-indicia portion in the test zone upon contact with a substrate. The device additionally includes a first polyol and a color differential enhancing component selected from the group consisting of an inhibitor to the enzyme and a competitive secondary substrate for the enzyme distributed throughout the non-indicia portion of the test zone.

Tissue Histology.

Antibodies may be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

IV. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments

Example 1

Materials and Methods

Screening.

Cell viability and apoptosis were assessed by CellTiter Glo (Promega) and ApoONE (Promega) kits, respectively. Molecular changes were screened using a MALDI-FTICR MS platform.

Multi-Omics Analysis.

Samples were analyzed for transcriptome changes by RNA sequencing at the Genomics Services Lab, Hudson-Alpha, for proteome changes by label free, SILAC, and phospho-enriched SILAC LC-MS/MS, and metabolome changes by UPLC-IM-MS and data-independent acquisition (MSE) using both hydrophilic-interaction liquid chromatography and reverse phase liquid chromatography.

Computational Analysis and Data Mining.

Data from all platforms were integrated and parsed for significantly changed, unique species. The inventors developed an analysis pipeline (manuscript in preparation) implemented in the Python programming language as part of the PySB modeling framework (Lopez et al., 2013). Bioservices (Cokelaer et al., 2013) was used to download pathways from the KEGG database (Kanehisa et al., 2012) that contain any proteins from a list of seed species. These pathways were combined to form a unified network based on common protein species. To examine the species-to-species interactions in the inventors' data networks, the inventors used the open source systems biology platform Cytoscape (Shannon et al., 2003), the QIAGEN IPA network analysis tool, and annotated literature.

Cell Culture.

Human lung carcinoma A549 cells were obtained from ATCC (Manassas, Va.) and cultured in Dulbecco's Modified Eagle's Medium (DMEM, Gibco) with 10% v/v heat-inactivated fetal bovine serum (Atlanta Biologicals) and 1% v/v penicillin/streptomycin (P/S) (Gibco) at 37° C. with 5% $CO_2$ atmosphere. Stable isotope labeling by amino acids in cell culture (SILAC) media were prepared using SILAC DMEM (Thermo Scientific) containing 10% v/v dialyzed heat-inactivated FBS (Fisher), 1% v/v P/S, proline (250 mg/L) (Thermo Scientific), and appropriate light and heavy labeled arginine (84 mg/L), lysine (146 mg/L). Cells were seeded to tissue-culture treated vessels at the following densities: 96-well plates, $1\times10^4$ cells per well in 95 µL; 24-well plates, $5\times10^4$ cells per well in 475 µL; 6-well plates, $2\times10^5$ cells per well in 3.1 mL; 100 mm dishes, $2\times10^5$ cells per dish in 10 mL; 100 mm flasks, $4\times10^6$ cells per flask in 20 mL. In all experiments, cells were cultured for 24 h prior to treatment with cisplatin or no treatment control.

For proteomic and metabolomic label-free analyses, five sterile indium tin oxide (ITO)-coated glass slides (Delta Technologies) were placed in a tissue culture flask with removable lid (TPP). Cisplatin (Tocris Bioscience) was added to a final concentration of 50 µM from a 4 mM stock. For proteomic analyses, slides were removed and washed 3 times with PBS, placed on dry ice, flash-frozen in liquid nitrogen, and stored at −80° C. prior to lysis. For metabolomics analysis, slides were washed in 50 mM ammonium formate.

For SILAC experiments, A549 cells were cultured in SILAC media for two weeks to ensure isotopic amino acid incorporation (verified by proteomic analysis). Cells were plated to 10 cm dishes and incubated with or without 50 µM cisplatin. Following treatment cells were washed 3 times with 4° C. PBS. For phospho-SILAC, cells were washed with 4° C. PBS containing 1 mM sodium orthovanadate.

Cell Viability and Apoptosis Assays.

Cisplatin (Tocris Bioscience) was serially diluted in water to generate a 20× stock plate representing the full spectrum of concentrations tested; 5 µL was applied per well containing 95 µL of cells in black-welled 96-well plates (Costar). At each time point, cell viability and apoptosis were assessed by CellTiter-Glo (Promega) and ApoONE (Promega) kits, respectively. Plates were incubated at 37° C. in a plate reader (BioTek) with data 174 acquisition every 10 min by luminescence (1 s read time, 200 gain) and fluorescence (485 nm excitation, 528 nm emission). Triton X-100 (Research Products International Corp) and staurosporine (Tocris Bioscience) were added as positive controls for CellTiter-Glo and ApoONE, respectively. Each assay was performed in triplicate wells in triplicate plates. Cell viability was also assessed using the LIVE/DEAD Viability/Cytotoxicity Kit for mammalian cells (ThermoFisher). Probes were added to the cells for 30 minutes at room temperature, and images were acquired using the fluorescein and rhodamine filter sets on the Olympus IX73.

Molecular Screening Assay.

Cells were seeded in 24-well plates and left untreated or were treated with cisplatin from 20× stocks. After incubation for the respective times, wells were washed 3 times with PBS and stored at −80° C. The effect of different toxin dosage amounts and exposure times on the molecular content of a sample may be evaluated and reported directly for thousands of molecular species based upon the mass spectra that were collected for each of the samples. A comparison of the mass-to-charge (m/z) peak content between spectra from dosed cells and a reference spectrum from a non-dosed control sample delivers a mass spectrometric assessment of toxicity-induced molecular variation. However, seeking a data-driven global comparison instead of focusing on specific molecular species of interest makes the assessment of molecular change between the different experimental conditions very complex and high-dimensional. To determine which dosage amount induces the greatest molecular change, the inventors developed a quick and broad assessment of toxicity-induced molecular variance summarizing the entire recorded mass range. This approach projects the high-dimensional variance between the spectra of different experimental conditions to a lower-dimensional representation, which allows the researcher to instantly assess overall molecular variance between different dosage conditions as a single scalar value.

Samples for rapid molecular screening analysis were prepared within the same 24-well cell culture plates in which they had been grown. Cells were first lysed with 100 µL of 25% methanol (MeOH) followed by reduction with 1 µL of 40 mM dithiothreitol (DTT) for 30 minutes at 37° C. Alkylation was performed with 2 µL of 80 mM iodoacetamide (IAA) for 30 minutes at room temperature in the dark. Subsequently, proteins were digested using 1 µL of 1 µg/µL Trypsin Gold, MS grade (Promega) for 3.5 h at 37° C. Trypsin was inactivated and digestion was stopped using 2 µL of 0.5% acetic acid. Protein digests were then transferred to PCR tubes and centrifuged to remove cell debris. Sample were desalted (EMD Millipore ZipTip, C18) and 300 nL of the cleaned up protein digests were spotted onto a MALDI anchor plate (Bruker) along with 300 nL of 10 mg/mL α-cyano-4-hydroxycinnamic acid (CHCA) in 50% acetonitrile (ACN), 0.1% trifluoroacetic acid (TFA). Screening analysis was performed using a Bruker 15T solariX MALDI FTICR mass spectrometer (Bruker Daltonics, Billerica, Mass., USA), which has mass resolution >100,000 and mass accuracy <2 ppm. The instrument is equipped with an Apollo II dual MALDI/ESI ion source and a Smartbeam II 2 kHz Nd:YAG (355 nm) laser. All data were collected using the small laser setting (~50 μm) with the instrument set to randomly "walk" between scans within each MALDI sample spot. Acquisition was <30 seconds/sample. Data were collected from m/z 400-5,000 with a resolving power of ~85,000 at m/z 1,000. Special tuning of the Funnel RF amplitude (190 Vpp), accumulation hexapole (1.4 MHz, 1200 Vpp), transfer optics (2 MHz, 305 Vpp), time of flight delay (1.5 ms), and ICR cell (sweep excitation power: 21%) were required for peptide analysis. External calibration was performed prior to analysis using cesium iodide (CsI) clusters. DataAnalysis 4.2 (Bruker Daltonics, Billerica, Mass., USA) was used to export spectra into a form compatible with the inventors' custom data processing scripts (standard XY ASCII).

Within each time point (represented by a 24-well plate), seven different dosage conditions were measured: six different toxin dosages and one reference condition (e.g., untreated). Per dosage condition there were nine distinct replicate measurements made: each dosage condition was represented by three replicate wells, from which three technical replicate spectra were measured per well. As a result, for each time point, seven dosage conditions with nine replicates amount to the acquisition of 63 MALDI FTICR mass spectra per 24-well plate. These spectra themselves are an average of 10 individual spectra that were acquired at random locations within a single MALDI spot, with acquisition at each location accumulating 500 laser shots per spectrum. The screening method first trimmed these 63 spectra to the relevant mass range of m/z 900 to 5000, yielding a data matrix of 63 rows×381,513 columns Each row captures a spectrum and each column reports a particular m/z bin across all spectra in this table. To ensure robustness against outlier measurements, the nine technical replicates per dosage condition were first normalized to each other and then summarized into a single representative spectrum for that dosage condition by taking the median spectrum across all nine normalized spectra. This step employed standard total ion current (TIC) based normalization. The resulting 7×381,513 data matrix contained a single consensus mass spectrum for each of the dosage conditions. The next step prepared the different dosage conditions for direct comparison by normalizing the seven spectra to each other, using the same TIC based normalization method that was applied across replicates in the previous step. The seven normalized spectra in the resulting 7×381,513 data matrix were now projected onto the same ion intensity scale, allowing for direct comparison of intensity values.

However, these spectra described the full profile across the entire mass range, whereas the inventors' screening method should focus only on the detected ion species and their peaks. Therefore, the spectra were translated into peak lists and their corresponding peak heights. To accomplish this, an R script mined peak locations along the m/z axis from an average spectrum of all seven spectra, recording any peak that surpassed a threshold of 1.7% of the highest recorded peak intensity. In all time points, this threshold returned ~4,000 individual ion peaks, ensuring a broad spread of contributing ion species into the inventors' overall molecular variance assessment. Retrieving peak intensities from the seven full profile spectra for each of these peak locations delivered a 7×~4,000 data matrix of peak intensities, which reports molecular content across different ion species for each of the seven dosage conditions. The final step of the screening procedure is to cast the ~4,000-dimensional difference between two such rows into a single summary 'molecular change' value without losing too much information. The first dimensionality reduction step uses principal component analysis (PCA) to project the seven measurements from a ~4,000-dimensional space (of which many dimensions are correlated) to a two-dimensional space in which the two dimensions are orthogonal and the axes represent the directions of highest variance. The second step is to calculate the distance between each pair of measurements in this two-dimensional space using the 'cosine' distance measure, which is actually one minus the cosine of the included angle between the measurement vectors. These steps are accomplished in MATLAB (The Mathworks Inc., Natick, Mass.) using the 'princomp' function for PCA projection and the 'pdist' function for the cosine distance calculation. The screening method then reports back the distance value between the reference measurement and each of the particular dosage measurements. These six distance values can be considered a representation of the molecular difference between a dosage measurement and the reference measurement, effectively reporting a relative measure for molecular variance for each dosage amount. Within a set of seven dosage conditions, these values show which dosage amount results in stronger molecular deviation from the reference. The molecular variance score reduces the information to a single objectively measured value that represents the magnitude of the perturbation induced by cisplatin comparable among all the dosing conditions tested.

Transcriptomics.

Cells were seeded in 6-well plates and incubated with or without 50 μM cisplatin for 1 h, 6 h, or 24 h. RNA was isolated using the RNeasy Mini Kit (Qiagen). For each time point, untreated and cisplatin-treated samples were isolated in triplicate and analyzed by the Genomics Services Lab at HudsonAlpha. RNAseq was performed using poly(A) selection on an Illumina HiSeq v4 sequencing platform. Reads were paired-end with a read length of 50 bp and 50 million reads per sample.

Proteomics—Label Free LC-MS/MS.

Cells were scraped from slides and lysed in 300 μL of 50 mM Tris pH 8, 150 mM NaCl, 1% Nonidet 40, 1 mM EDTA with added HALT Protease Inhibitor Cocktail (Thermo Scientific), centrifuged, and assayed for protein concentration (BCA Protein Assay, Thermo Scientific Pierce) using a SpectraMax M2e Microplate Reader with SoftMax Pro software version 5 (Molecular Devices). Aliquots of 100 μg of protein were acetone precipitated in six times the volume for 2 h at −80° C. Precipitates were washed three times with cold acetone and reconstituted in 10 μL of neat trifluoroethanol (TFE) and 10 μL of 100 mM Tris (pH 8.0). Samples were reduced with 1 μL of 0.5 M Tris(2-carboxyethyl)phosphine hydrochloride (TCEP) for 30 minutes at room temperature and alkylated with 2 μL of 0.5 M IAA for 30 minutes at room temperature in the dark. Samples were diluted with 100 mM Tris (pH 8.0) to obtain a final solution containing 10% TFE. The samples were digested with 2 μg of trypsin (a ratio of 50:1 protein 273 to enzyme) overnight at 37° C. A solution of 60% formic acid (FA) was added to the samples until they reached pH 3. Aliquots of 5 μg of digested sample were desalted using C18 spin tips (Protea) according to the supplied protocol and dried samples were reconstituted in 15 μL of 0.1% FA. Five replicates of cisplatin treated and control (untreated) cells were prepared in parallel.

Samples were analyzed on a Thermo Scientific Orbitrap Fusion Tribrid mass spectrometer in line with a Thermo Scientific Easy-nLC 1000 UHPLC system. Samples, 2 µL, were injected via the autosampler and loaded onto a Thermo Scientific Acclaim PepMap 100 C18 UHPLC column (75 µm×250 mm, 2 µm particle size, 100 Å pore size), with 0.1% FA in water (mobile phase A). Peptides were separated over a 140 minute two-step gradient with initial conditions set to 100% mobile phase A for 5 minutes before ramping to 20% mobile phase B, 0.1% FA in ACN, over 100 minutes and then 32% mobile phase B over 20 minutes. The remainder of the gradient was spent washing at 95% mobile phase B and returning to initial conditions. Eluted peptides were ionized via positive mode nanoelectrospray ionization (nESI) using a Nanospray Flex ion source (Thermo Fisher Scientific). The mass spectrometer was operated using a 3 second top speed data-dependent acquisition mode. Fourier transform mas spectra (FTMS) were collected using 120,000 resolving power, an automated gain control (AGC) target of 200,000, and a maximum injection time of 50 ms. Precursor ions were filtered using monoisotopic precursor assignment according to charge state (9>z>1 required). Previously interrogated precursor ions were excluded using a 30 s dynamic window (±10 ppm). Precursor ions for tandem mass spectreomtry (MS/MS) analysis were isolated using a 1.5 m/z quadrupole mass filter window. Precursor ions were fragmented via higher energy dissociation (HCD) using a normalized collision energy of 35%. Ion trap fragmentation spectra were acquired using an AGC target of 1,000 and maximum injection time of 40 ms. Data were analyzed via Protalizer (Vulcan Analytical Inc.) to identify proteins and determine a-fold change in proteins common to the treated and control samples. Search parameters were set to include carbamidomethyl, phosphorylation, and oxidation modifications, as well as methionine-containing and miscleaved peptides (maximum of two miscleavages). Both peptide and protein target FDR rates were set to 1%. For the Orbi-trap-LTQ, data precursor and fragment tolerances were 20 ppm and 0.6 Da respectively. For Orbitrap-Orbitrap data precursor and fragment ion tolerances were both 20 ppm. Changes in protein abundance were considered statistically significant at an absolute value of 1.5 or above and a p-value of ≤0.1.

SILAC LC-MS/MS.

Cells grown in SILAC media (as described above) were lysed in 500 µL of 50 mM Tris pH 8, 150 mM NaCl, 1% Nonidet 40, 1 mM EDTA with added HALT Protease/Phosphatase Inhibitor Cocktail (Thermo Scientific), centrifuged at 15,871×g for 10 min at 4° C., and assayed as detailed above for protein concentration (BCA, Pierce). Aliquots of 50 µg of protein from heavy and light labeled cell lysates (representing control and treated exposures) were mixed 1:1. The combined lysate was then precipitated in six times the volume of ice-cold acetone overnight at −20° C. Following precipitation, samples were centrifuged at 18,000×g at 4° C., and precipitates were washed with cold acetone, dried, and reconstituted in 100 mM Tris pH 8, containing 50% TFE. Samples were digested as described for label-free samples. Two replicates of cisplatin treated and control cells were prepared per time point. Replicates represented a label-swap with one replicate as heavy-cisplatin treated, light-control and the other as light-cisplatin treated, heavy-control.

Samples were analyzed by LC-MS/MS on a QExactive mass spectrometer (Thermo Scientific) coupled to an Eksigent NanoLC. Peptides were loaded onto a self-packed biphasic C18/SCX MudPIT column using a Helium-pressurized cell (pressure bomb). The MudPIT column consisted of 360×150 µm i.d. fused silica, which was fitted with a filter-end fitting (M-120, IDEX Health & Science) and packed with 6 cm of Luna SCX material (5 µm, 100 Å, Phenomenex) followed by 4 cm of Jupiter C18 material (5 µm, 300 Å, Phenomenex). Once the sample was loaded, the MudPIT column was connected using an M-520 microfilter union (IDEX Health & Science) to a laser-317 pulled emitter analytical column (360 µm×100 µm i.d.) packed with 20 cm of C18 reverse phase material (Jupiter, 3 µm, 300 Å, Phenomenex). MudPIT analysis was performed with an 11-step salt pulse gradient (25, 50, 75, 100, 150, 200, 250, 300, 500, 750, and 1000 mM ammonium acetate). Following each salt pulse, peptides were gradient-eluted from the reverse phase analytical column at a flow rate of 500 nL/minute, and the mobile phase solvents consisted of 0.1% FA in water (solvent A) and 0.1% FA in ACN (solvent B). A 120-min reverse phase gradient was used consisting of 2-50% solvent B in 105 minutes followed by a 15 minute equilibration at 2% solvent B for the peptides from the first 10 SCX fractions. For the last fraction, the peptides were eluted from the reverse phase analytical column using a gradient of 2-98% solvent B in 105 minutes. Peptides were introduced into the mass spectrometr via nano-electrospray ionization. The Q Exactive was operated in the data-dependent mode acquiring HCD MS/MS scans (R=17,500) after each MS1 scan (R=70,000) on the 20 most abundant ions using an MS1 ion target of 1×106 ions and an MS2 target of 1×105 ions. The maximum ion time for MS/MS scans was set to 100 ms, the HCD-normalized collision energy was set to 30, dynamic exclusion was set to 30 s, and peptide match and isotope exclusion were enabled.

Data were analyzed via MaxQuant software package, version 1.3.0.5 to determine protein identification and -fold change differences between common proteins in the treated and control samples. MS/MS spectra were searched against a human subset database created from the UniprotKB protein database. Precursor mass tolerance was set to 20 ppm for the first search, and for the main search, a 10-ppm precursor mass tolerance was used. The maximum precursor charge state was set to 7. Variable modifications included carbamidomethylation of cysteine (+57.0214) and oxidation of methionine (+15.9949). Enzyme specificity was set to Trypsin/P, and a maximum of two missed cleavages were allowed. The target-decoy false discovery rate (FDR) for peptide and protein identification was set to 1% for peptides and 1% for proteins. A multiplicity of 2 was used, and Arg10 and Lys8 heavy labels were selected. For SILAC protein ratios, a minimum of two unique peptides and a minimum ratio count of 2 were required, and the requantify option was enabled. Protein groups identified as reverse hits were removed from the datasets, along with non-human contaminants and identifications to which multiple proteins were assigned. To determine significance of-fold change for the quantified proteins, the inventors followed the methods outlined in Thissen et al. (2002). Briefly the mean and standard deviation were calculated for the log 2 value of the normalized heavy/light ratio. Next a p-value was calculated from the distribution of these log 2 values. The data were ranked by p-value and sorted in descending order. The Benjamini-Hochberg formula was applied and data with corresponding p-values less than the resulting Benjamini-Hochberg value were determined to have statistical significance. Protein groups containing non-human proteins and multiple proteins were excluded from further analysis. For networking and analysis purposes, a final step was performed to determine if proteins were considered significantly changed or unchanged. Proteins were considered significantly changed if they displayed a significant change in the same direction in both label-swapped replicates, if they displayed a significant change in one replicate and an insignificant change (-fold change>|1.5|) in the same direction in the other replicate, or if they displayed a significant change and were found in only one replicate. Proteins that displayed a significant change in opposite directions in each replicate or displayed a significant change in one replicate but were unchanged in the other replicate were not considered significantly changed.

ph-SILAC LC-MS/MS.

For phospho-enrichment SILAC cells grown in SILAC media were lysed in 500 µL of 50 mM Tris pH 8, 150 mM NaCl, 1% Nonidet 40, 1 mM EDTA, 1 mM PMSF, centrifuged at 15,871×g for 10 minutes at 4° C., and the supernatant was assayed for protein concentration. Aliquots of 900 µg of protein from heavy and light labeled cell lysates were mixed 1:1. To each sample was added an equal volume of neat TFE. Samples were reduced for 30 minutes at room temperature with 1 µL of 0.5 M TCEP per 100 µg of sample and then alkylated for 30 minutes at room temperature in the dark with 2 µL of 0.5 M IAA per 100 µg of sample. Samples were diluted with 100 mM Tris to a final volume of 10 times the amount of TFE added and the samples were digested with trypsin at a ratio of 25:1 protein to enzyme overnight at 37° C. TFA was added to the samples until they reached pH 3. Digested samples were desalted using Waters Sep-Pak Light C18 cartridges (130 mg) and a vacuum assisted solid-phase extraction manifold (Supelco). Samples were diluted with an equal volume of 0.1% TFA to dilute the concentration of TFE to below 5%. Columns were conditioned with 5 mL of 100% ACN and equilibrated with 3×5 mL of 0.1%

TFA. Samples were loaded at 1-2 mL/min and washed with a volume of 0.1% TFA equal to the pre-diluted sample volume. Bound peptides were eluted at 1-2 mL/min with sequential 1 mL aliquots of 10%, 15%, 20%, 25%, 35%, 368 40%, and 60% ACN each containing 0.1% TFA. The eluate was divided among eight tubes and then dried at ambient temperature using a SpeedVac concentrator (Thermo Scientific).

Samples were enriched for phosphopeptides using $TiO_2$ beads. Two 30 mg aliquots of $TiO_2$ beads were washed three times with 300 mg/mL lactic acid in 80% ACN, 20% water, 0.05% heptafluorobutryic acid (HFBA). Each of the eight desalted dried fractions were reconstituted in 250 µL of 300 mg/mL lactic acid in 98% water, 2% ACN, 0.05% HFBA and combined; 1 mL of sample was incubated with each aliquot of $TiO_2$ beads for 30 minutes with mixing (to bind phosphopeptides) and centrifuging before the supernatant was removed. The beads were washed with 500 µL of 80% ACN, 20% water, 0.05% HFBA for 5 minutes. The supernatant was removed, and the beads were washed two times for 5 minutes with 500 µL of 300 mg/mL lactic acid in 80% ACN, 20% water, 0.05% HFBA. Finally the beads were washed three times with 500 µL of 80% ACN, 20% water, 0.05% HFBA. Bound peptides were eluted into three fractions. The beads were first incubated with 500 µL of 0.5 M $NH_4OH$ for 5 minutes, and then incubated twice with 500 µl of 5 M $NH_4OH$ for 5 minutes. Samples were dried and each of the three fractions were reconstituted in 20 µL of 0.1% FA and the fractions combined prior to LC-MS/MS analysis. Two replicates of cisplatin treated and control cells were prepared. Replicates represented a label-swap with one replicate as cisplatin treated-heavy, control-light and the other as cisplatin treated-light, control-heavy.

Samples were analyzed on a Linear Trap Quadrupole-Orbitrap Velos (Thermo Scientific) in line with an Eksigent NanoLC. Phosphopeptides were loaded on a MudPIT column as described above for SILAC peptides. An 8-step salt pulse gradient (25, 50, 75, 100, 150, 250, 500, and 1000 mM ammonium acetate) was performed. Following each salt pulse, peptides were gradient-eluted from the reverse phase analytical column at a flow rate of 500 nL/minute, and the mobile phase solvents consisted of 0.1% FA in water (solvent A) and 0.1% FA in ACN (solvent B). A 120-min reverse phase gradient was used that consisted of 2-40% solvent B in 105 min followed by a 15 min equilibration at 2% solvent B for the peptides from the first seven SCX fractions. For the last fraction, the peptides were eluted from the reverse phase analytical column using a gradient of 2-98% solvent B in 105 minutes. Peptides were introduced into the mass spectrometer via nano-electrospray ionization into the mass spectrometer and the data were collected using a 17-scan event data-dependent method. Full scan (m/z 350-2000) spectra were acquired with the Orbitrap as the mass analyzer (resolution, 60,000), and the 16 most abundant ions in each MS scan were selected for fragmentation in the Velos ion trap. An isolation width of 2 m/z, activation time of 10 ms, and 35% normalized collision energy were used to generate tandem mass spectrometry spectra.

The data were analyzed as described for SILAC data with two differences: 1) variable modifications also included phosphorylation of serine, threonine and tyrosine (+79.9663) and 2) the target-decoy false discovery rate (FDR) for identification was set to 1% for peptides and 2% for proteins. A minimum ratio count of 2 were required, and the requantify option was enabled. Prior to evaluating significance, all rows with missing H:L normalized values and reverse hits were removed. Significance of the -fold change for peptides was determined as described above for SILAC proteins. All non-human hits were removed, and no additional filtering of phosphopeptides was performed. For networking and analysis purposes, a final step was performed to determine if proteins were considered significantly changed or unchanged. In cases where unique peptides had multiple hits, -fold change values for all hits within a replicate (heavy or light treated) were averaged and the overall significance of the combined values evaluated as higher or lower than 50% true. If a peptide had a low percent true value (<50%) in both replicates it was considered unchanged. If a peptide had a high percent true value (>50%) in both replicates it was considered as follows: peptides were considered significantly changed if they 1) displayed a significant change in the same direction in both label-swapped replicates, 2) displayed a significant change in one replicate and an insignificant change (-fold change>|1.5|) in the same direction in the other replicate, or 3) displayed a significant change and were found in only one replicate; peptides that displayed a significant change in opposite directions in each replicate or displayed a significant change in one replicate but were unchanged in the other replicate were not considered significantly changed. Significantly changed unphosphorylated peptides measured in the ph-SILAC experiments were grouped with the SILAC data.

Metabolomics.

All solvents used for metabolite extraction and analysis (MeOH, $H_2O$, ACN, FA, ammonium formate and ammonium acetate) were LC/MS grade (Fisher Scientific, Fair Lawn, N.J.). Cell slides (~6-7×$10^3$ cells/slide) were kept at −80° C. or dry ice until ready for metabolomic sample processing. Intracellular metabolites were extracted by scraping individual cell slides in 350 µL of cooled (4° C.)

2:2:1 (v:v:v) ACN:MeOH:H$_2$O. Individual samples were dried in vacuo just until dried and reconstituted in 1 mL of 75:25 (v:v) ACN:H2O (dry ice cooled), vortexed for 30 s, sonicated (five 1 s pulses at 30% amplitude while on ice) and incubated at −80° C. for 2 h. After incubation, samples were cleared by centrifugation at 15,000 rpm for 15 min, and the resulting supernatant was removed, halved in volume and evaporated to dryness in a vacuum concentrator. Dried extracts were reconstituted in 100 µL of reverse phase reconstitution solvent mixture containing 98:2 (v:v) H$_2$O: ACN with 0.1% FA for reverse phase analysis or 100 µL of normal phase reconstitution solvent mixture containing 80:20 (v:v) ACN:H2O for normal phase analysis; followed by centrifugation for 60 s at 5,000 rpm to remove insoluble debris. Quality control samples were prepared by combining equal volumes (20 µL) of each sample type and samples were transferred to HPLC vials prior to IM-MS analysis.

Metabolomic Mass Spectrometry Analysis.

UPLC-IM-MS and data-independent acquisition (MSE) were performed on a Synapt G2 HDMS (Waters Corporation, Milford, Mass.) mass spectrometer equipped with a nanoAcquity UPLC system and autosampler (Waters Corporation, Milford, Mass.). Chromatographic separations were achieved using both hydrophilic-interaction liquid chromatography (HILIC) and reverse phase liquid chromatography (RPLC). A 1.7 µm (1 mm×100 mm) ACQUITY BEH amide column (Waters Corporation) was used for HILIC analysis and reverse phase liquid chromatography was performed using a 1.8 µm (1 mm×100 mm) HSS T3 ACQUITY column fitted with a 1.8 µm HSS C18 pre-column (2.1 mm×5 mm) Samples were analyzed three times each in UPLC-HILIC-HDMSE and UPLC-RPLC-HDMSE in positive ionization mode. For HILIC analysis, mobile phase A was 9:1 (v:v) H$_2$O:ACN and mobile phase B was 9:1 (v:v) ACN:H$_2$O, both with 0.1% FA and 10 mM ammonium acetate. The following elution gradient was used for HILIC analysis: 0 min, 12.5% A; 1 min, 12.5% A; 4 min, 62.5% A; 10 min, 37.5% A; 11 min, 80% A; 13 min, 80% A; 14 min, 12.5% B. Flow rates for HILIC analysis were 90 µL/min with a column temperature at 30° C. and an injection volume of 5 µL. For RPLC analysis, mobile phase A was H$_2$O and mobile phase B was ACN, both with 0.1% FA. The following elution gradient was used for RPLC analysis: 0 min, 99% A; 1 min, 99% A; 10 min, 40% A; 20 min, 99% A; 22 min, 99% A; 25 min, 1% A. Flow rates for RPLC analysis were 75 µL/min with a column temperature of 45° C. and an injection volume of 5 µL.

HDMSE analyses were run using resolution mode, with a capillary voltage of 3 kV, source temperature at 120° C., sample cone voltage at 35V, source gas flow of 300 mL min-1, desolvation gas temperature of 325° C., He cell flow of 180 mL min-1, and an IM gas flow of 90 mL min-1. The data were acquired in positive ion mode from 50 to 2000 Da with a 1 s scan time; leucine enkephalin was used as the lock mass (m/z 556.2771). All runs were analyzed using HDMSE with an energy ramp from 10 to 40 eV.

Metabolite Data Processing and Analysis.

The acquired UPLC-IM-MSE data were imported, processed, normalized and interpreted in Progenesis QI v.2.1 (Non-linear Dynamics, Newcastle, UK). Briefly, each UPLC-IM-MSE data file was imported as an ion intensity map (used for visualization in both m/z and retention time dimensions) and underwent retention time alignment and peak picking. Peak picking was performed on individual aligned runs by matching peaks in an aggregate data set that is created from all aligned runs. Following peak picking, the features (retention time and m/z pairs) were reduced using both adduct ([M+H]+, [M+Na]+, [M+K]+, etc.) and isotope deconvolution. Data were normalized to all compounds. Statistically significant changes were identified using multivariate statistical analysis 458 including principal component analysis (PCA) and p-values generated using analysis of variance (ANOVA) or pairwise comparisons. Pairwise comparisons were performed for each cisplatin treatment (1, 6, 24 or 48 hr) vs. its 460 matched control (1, 6, 24 or 48 hr). Three biological and three technical replicates from each sample type were used to calculate both-fold change and p-value and features were considered for identification only if they met both significance criteria of fold change >|1.5| and p≤0.1; the inventors have termed this list 'prioritized metabolites'. Prioritized metabolites or features were assigned tentative structural identifications using accurate mass measurements (<10 ppm error) and isotope distribution by searching the Human Metabolome Database (HMDB). Following tentative structural identifications for both chromatography methods (HILIC and RPLC), spreadsheets were merged for further data processing. In particular, metabolites associated with drugs, plants, food, and microbial origin were eliminated. Metabolites with a tentative structural identification (met the dual significance criteria of-fold change at an absolute value of 1.5 or above and a p-value of ≤0.1) were used in the mechanism of action. In an effort to increase the confidence in metabolite assignment, fragmentation spectra of metabolites that met significance criteria were searched in HMDB, METLIN, MassBank, and NIST. Metabolite peak identifications were putatively assigned using product ions observed in the fragment ion spectra analyzed in HDMSE mode. Ion mobility separations were used to isolate precursor ions and correlate product ions.

Computational Analysis.

Figure 4:
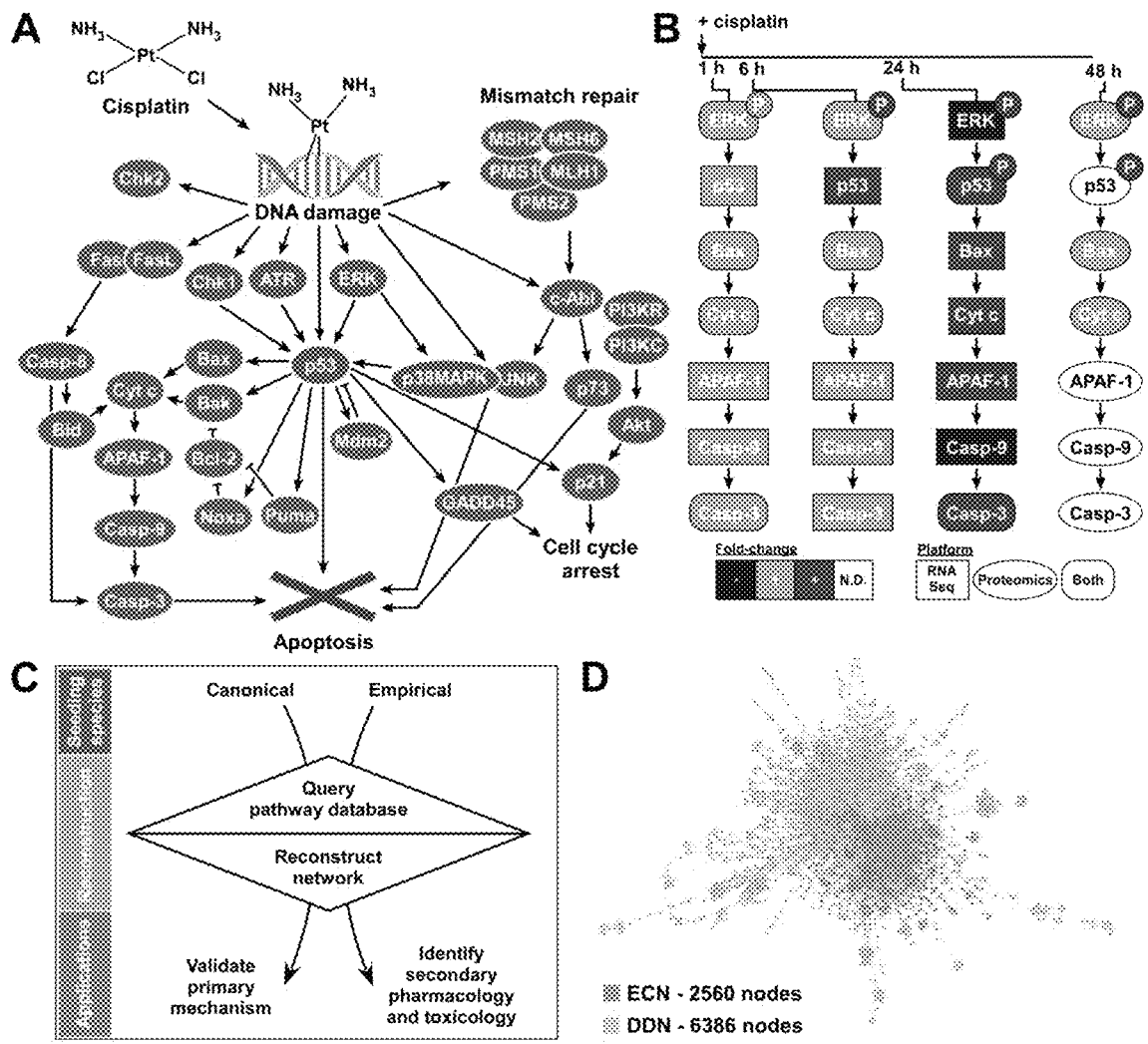
FIGS. 4A-D. Phase 3: Mechanism construction (days 26-30).

Data from all platforms were integrated and parsed for significantly changed, unique species for comparison against the canonical cisplatin mechanism and for network analysis. The inventors developed an analysis pipeline (manuscript in preparation) implemented in the Python programming language as part of the PySB modeling framework. Bioservices 30 was used to download pathways from the KEGG database (retrieved Nov. 26, 2015) that contain any proteins from a list of seed species. These pathways were then combined to form a unified network based on common protein species. Using this approach, the inventors built three distinct networks. The expanded canonical network (ECN) was based on species in the cisplatin canonical mechanism (FIG. 4A). The expanded resistance network (ERN) was based on seed species involved in cisplatin resistance collated from a literature search. The data driven network (DDN) was based on significantly changed, unique species measured in the high-dimensional -omics data. Venn diagrams were made using eulerAPE.

Data Mining.

To examine the species-to-species interactions in the inventors' data networks, they used the open source systems biology platform Cytoscape. The data network was uploaded and queried by selecting a species of interest and viewing first-degree neighbors. Once connections were formed between species, pathways took form that were supported by using the QIAGEN IPA network analysis tool and annotated literature.

Example 2

Results and Discussion

This study validates a multi-omics platform designed to assess the comprehensive MOA of exogenous compounds in 30 days. The inventors considered selection of cell type, exposure methods, and analytical modalities by evaluating stability, reproducibility, utility, and feasibility within 30 days. For this study, they used A549 cells; however, their platform is amenable to various adherent and suspension cell lines. The sponsoring agency selected cisplatin as the test compound and revealed its identity on the first day of the 30-day period.

FIG. 1 graphically illustrates the three phases of the procedure: 1) molecular screening (days 0-3), 2) discovery analytics (days 4-25), and 3) mechanism construction (days 26-30). Phase 1 screens a wide range of cisplatin dose and exposure times to establish the treatment protocol for discovery experiments. This preliminary screen deduces exposure conditions that provide relevant data for the MOA, allowing the application of this protocol to uncharacterized compounds. During Phase 2, transcriptomics, proteomics, and metabolomics determine changes in molecular expression correlated with exposure to the compound. In Phase 3, data integration and analysis drive mechanism construction.

Phase 1: Preliminary Screening Determines Relevant Dose and Exposure Time.

Figure 2:
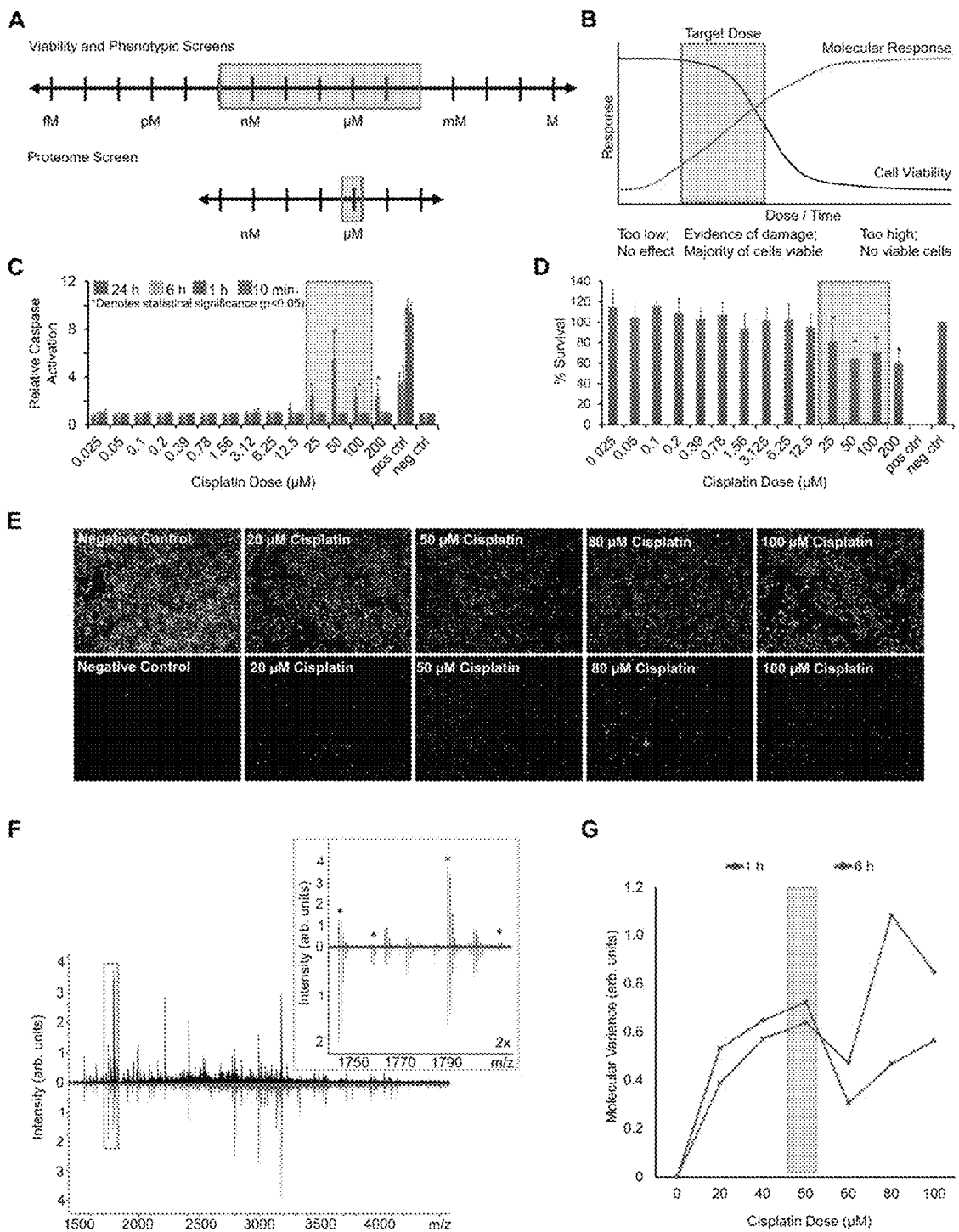
FIGS. 2A-G. Phase 1: dose screening (days 0-3).
Figure 3:
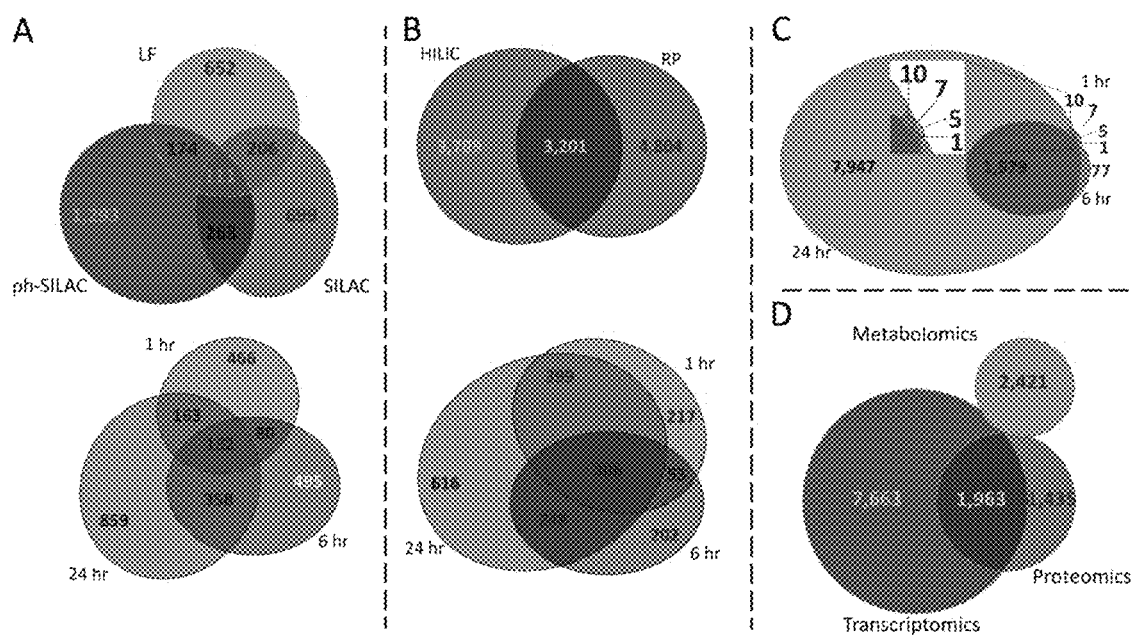
FIGS. 3A-D. Phase 2: Discovery results (Days 4-25).

To make the analysis strategy applicable to uncharacterized compounds, it does not rely on previous experimental data to establish an exposure dose. The inventors hypothesized that a preliminary screening process (FIGS. 2A-G) could select optimal treatment conditions for Phase 2 omics experiments. FIG. 2A illustrates the two-stage screening protocol. First, a set of assays that indicate physiological perturbations (e.g., cell viability, cell cycle arrest, oxidative stress, etc.) narrows the possible dose range to a small number of conditions. Second, mass spectrometry (MS) analysis of proteome changes within this limited dose range leads to the selection of a single exposure condition for all subsequent experiments. The optimal dose, conceptualized in FIG. 2B, elicits maximum molecular response while preserving >50% cell viability.

During Stage 1 of the screening experiment, the inventors monitored dose-dependent caspase 3/7 activation (FIG. 2C), ATP levels (FIG. 2D), and cell viability (FIG. 2E). The inventors analyzed 14 doses (0.025-200 µM) for cisplatin exposure times of 1, 6, and 24 h, with some selected measurements at 48 and 96 h. Based on the results obtained on day 1, the dose range of 20-100 µM was prepared for molecular screening.

For Stage 2, the inventors developed a rapid proteome screen using matrix-assisted laser desorption ionization (MALDI) MS to evaluate the magnitude of the molecular response. This assay determines changes in MS profiles at selected conditions compared to control, ensuring maximum opportunity to observe significant molecular changes in the discovery phase. To maximize throughput, the inventors focused on profile changes rather than identifications, avoiding the use of chromatography and tandem MS. These results titrated the cisplatin dose used in later experiments but were not used in the construction of the cisplatin MOA.

FIG. 2F shows representative mass spectra from this experiment—a 6 h exposure of 50 µM cisplatin and a vehicle control. Each peptidic profile contained >4,000 unique mass-to-charge (m/z) peaks to monitor for intensity changes across exposure conditions. To determine which cisplatin dose induced the greatest molecular change, the inventors developed a quantitative, automated approach to determine a molecular variance score—a metric that projects the high-dimensional variance between the spectra of different experimental conditions to a lower-dimensional representation using a principle component analysis. These details are in the supplemental methods.

FIG. 2G shows the molecular variance score for each cisplatin dose measured at 1 and 6 h. Only exposure times <24 h were analyzed during the molecular screen to maintain an efficient screening period (≤3 days). The inventors observed an increase in molecular variance with increasing cisplatin dose up to 50 µM; greater doses did not show a correlated response. This instability in the molecular variance score at doses >50 µM at 1 and 6 h corresponds with the variation seen in the caspase activation assay in the same dose range at 24 h (FIG. 2C). In both the physiological and molecular screen, 50 µM cisplatin elicits a maximum response and maintains cell viability of >50%, indicating an optimal dose of 50 µM cisplatin for discovery experiments.

This screen-determined concentration compares with reports of cisplatin-induced apoptosis and cytotoxicity; exposure doses range from 3.3-1000 µM (FIG. 8), and the $IC_{50}$ for A549 cells is 18-64 µM (Yang et al., 2013; Zhang et al., 2015). The molecular screen confirmed cisplatin-induced toxicity is measurable at 50 µM and as early as 1 h. These results support the inventors' hypothesis that a preliminary screen can determine optimal treatment conditions for an unknown compound, and they validate the inventors' established workflow.

Phase 2: A Multi-Omics Platform Captures Cisplatin-Induced Molecular Perturbations.

During the discovery phase, the inventors acquired comprehensive molecular data from transcriptome, proteome, phosphoproteome, and metabolome measurements of A549 cells treated with 50 µM cisplatin for 1, 6, 24 and 48 h. In total, they collected 254,470 measurements. Of the 53,500 unique, individual species detected, 13,483 were significantly changed (24%). FIGS. 3A-D, 9A-C, and 10A-B show the data generated by these modalities. Integration of data from these platforms facilitated the de novo, time-resolved MOA construction described below.

Phase 3: Mechanism Construction: Comparison of the Empirical Data to a Canonical Cisplatin Mechanism.

To evaluate their dataset, the inventors generated a canonical MOA consisting of 33 species from a literature survey of transcripts, proteins, and metabolites that change in a variety of cell lines exposed to cisplatin for less than 48 h (data not shown). FIG. 4A shows the constructed canonical mechanism; cisplatin-induced DNA damage initiates a cellular response that ends in apoptosis. The inventors' multi-omics platform detected 97% of the species in the canonical cisplatin MOA (all excepting Mdm2), and 82% of these changed significantly (data not shown).

FIG. 4B illustrates time-resolved data for an intrinsic apoptosis pathway within the canonical mechanism. Phosphorylation at Thr202 and Tyr204 activates ERK1; the homologous motif on ERK2 is Thr185/Tyr187. Phosphorylated ERK1 and/or ERK2 increased at each time point. Activated ERK can phosphorylate and activate p53 at multiple sites, including Ser392 (Cheng et al., 2008), which increased significantly in cisplatin-treated cells beginning at 24 h. The literature shows that p53 binds DNA as a tetramer, and phosphorylation at Ser392 enhances tetramer formation 10-fold (Sakaguchi et al., 1997). Additionally, Chk1 or Chk2 can phosphorylate p53 at Ser313/Ser314. The inventors' data show that p53 pSer313, pSer314 and/or pSer315 increased significantly in cisplatin-treated cells starting at 6 h. Phosphorylation at these sites can activate BAX (Ou et al., 2005) consistent with increased detection of the BAX transcript in cisplatin-treated cells at 24 h. In intrinsic apoptosis, Bax conformational change in the mitochondrial membrane contributes to cytoplasmic release of Cyt c (CYCS) leading to assembly of the apoptosome, which includes APAF-1 and Casp-9, and subsequent Casp-3 activation (Taylor et al., 2008). The inventors observed transcriptional upregulation in BAX, CYCS, APAF1, and CASP3 but not proteomic abundance changes for these species, consistent with mediation of their MOA through conformational changes, localizations, and cleavage events. Due to the central role of Casp-9 in the caspase cascade (Slee et al., 1999), downregulation of CASP9 at 24 h is consistent with a subpopulation of cells initiating anti-apoptotic pathways. By 48 h, none of the downstream apoptosis proteins changed significantly, suggesting that surviving cells were not initiating apoptosis.

Comparison of the Empirical Data to Expanded Mechanisms.

Comparison of the measured data to the literature-derived canonical MOA demonstrates agreement both in the network and on a time-resolved basis. However, the capture of 32 out of 33 species from >53,000 unique measurements tests less than 0.1% of the collected data. Thus, further validation of the inventors' approach required a strategy that expands beyond the current literature.

The inventors constructed networks by seeding with inputs based on annotated biology, with expansion informed by curated pathways from the Kyoto Encyclopedia of Gene and Genomes (KEGG) (Kanehisa et al., 2012), allowing the inventors' to validate their empirical findings against expected outcomes. The comprehensive nature of multi-omics datasets can surpass previously described MOAs. Therefore, the inventors hypothesized that seeding the empirically captured dataset would allow the inventors to move beyond these limits and permit exploration of previously unknown but important cellular and pharmacological events associated with the exposure conditions. FIG. 4C illustrates this concept. The inventors developed two networks to validate and interrogate their empirical dataset: the expanded canonical network (ECN), seeded with species from the canonical mechanism (data not shown), and the data-driven network (DDN), seeded with unique significantly changed species from the inventors' empirical data, 11,061 species (data not shown).

Figure 11:
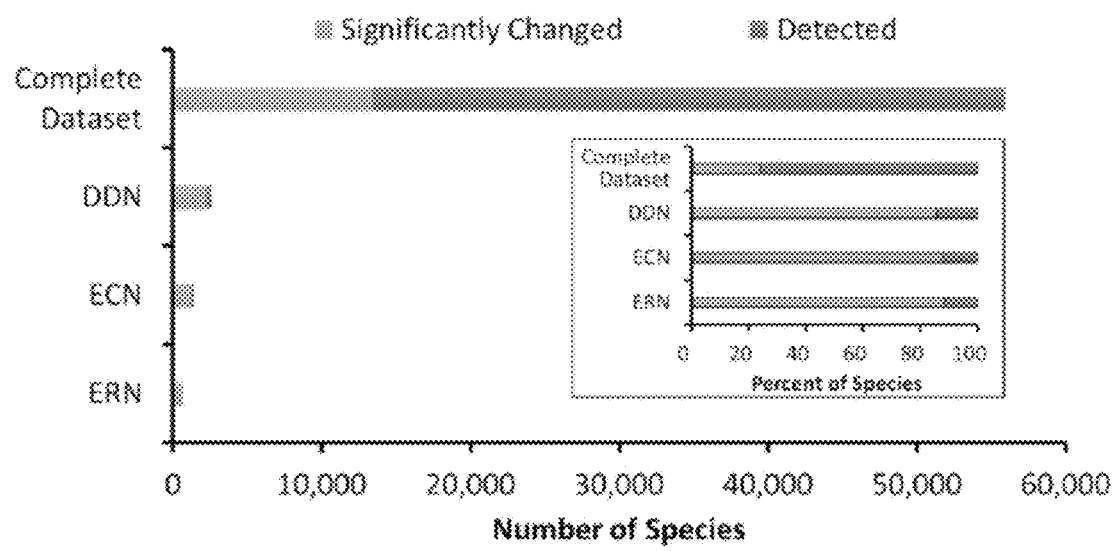
FIG. 11. Significant changes across datasets (related to FIGS. 4D and 5C). This graph shows the number of unique significant changes overlaid with the number of unique species detected in the complete, empirical dataset (55,898; 13,483 significant changes), the DDN (2,583 detected out of 6,386 species; 2,215 significant changes), the ECN (1,397 out of 2,560 species; 1,229 significant changes), and the ERN (667 out of 1,236 species; 589 significant changes). The inset shows the percentage of detected species that changed significantly.

The ECN contained 2,560 unique species (FIG. 4D). The inventors' multi-omics dataset captured 1,397 of these (55%), of which 1,229 changed significantly. The percentage of unique species that changed significantly in the ECN, 88%, is approximately 3.5-fold higher than the percentage of significantly changed species in the empirical dataset (FIG. 11). This value is also similar to the percent of significantly changed species determined for the canonical mechanism, validating the primary MOA on the scale of thousands of species and revealing the relevance of the ECN to the cisplatin MOA. Still, the significantly changed multi-omics data contains 80% more species than the ECN, providing the opportunity to investigate unexplored pathways related to cisplatin treatment. The inventors hypothesized that these additional measurements revealed previously described and novel off-target effects of cisplatin, including resistance mechanisms.

Figure 12:
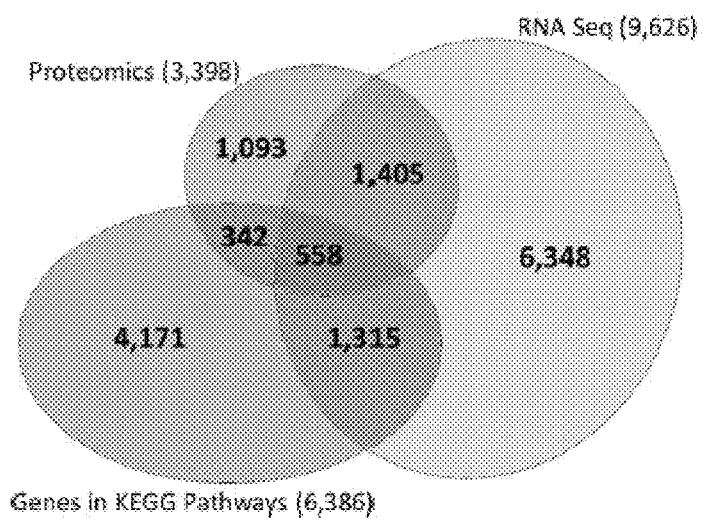
FIG. 12. Coverage of KEGG by the data-driven network (related to FIGS. 4D and 5C). The number of species (unique by gene symbol) are shown as measured by proteomics (red), RNAseq (green) and present with interaction information in the KEGG pathway database (purple). The overlap between species present in KEGG and measured proteins (26.5%) and measured transcripts (19.5%) is relatively low, indicating large numbers of molecular players for which prior functional knowledge is not available from KEGG.

The resulting DDN had 6,386 species (data not shown). The inventors experimentally measured 2,583 (40%) of these species, 2,215 of which were significantly changed. Similar to the ECN, 86% of the detected species within the DDN changed significantly (FIG. 11). For the DDN, limitations to KEGG precluded seeding with metabolomics data and limited the transcriptomic and proteomic data to the 2,215 species that were in KEGG (FIG. 12). FIG. 4D shows the ECN and DDN, with a total of 2,560 species (nodes) overlapping. The uncovered DDN region represents intracellular responses not currently understood in the context of cisplatin. As hypothesized, the empirical dataset provides the opportunity to explore novel secondary mechanisms.

Beyond the Primary MOA: Capturing the Dynamic Processes that Govern Cell Fate.

To complement the DDN analysis and investigate the capability of their platform to capture events outside of the primary MOA, the inventors threaded the empirical data through the Qiagen IPA causal network analysis tool and analyzed for pathways present at every time point. The inventors selected the HUWE1 pathway (Zhong et al., 2005) for further analysis since it appeared as one of the top five ranked hits at every time point and was the top hit at 6 h. The HUWE1 network contained a number of empirically measured species that revealed significant -fold changes over time.

Figure 5:
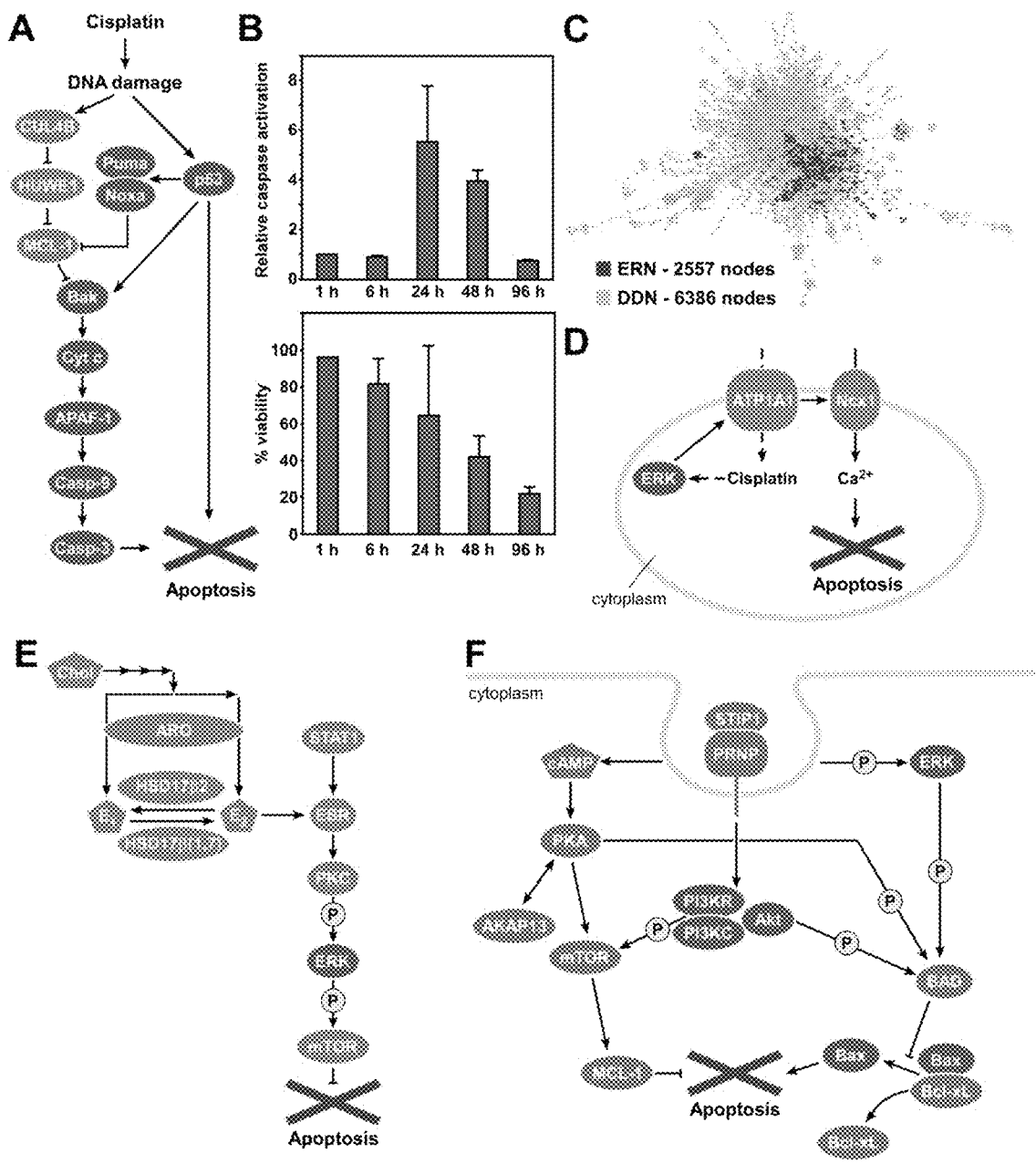
FIGS. 5A-F. Beyond the primary MOA.

HUWE1 is an E3 ubiquitin ligase that modulates DNA damage response and apoptosis pathways upon genotoxic stress (Thong et al., 2005). HUWE1 targets MCL-1, an anti-apoptotic Bcl2 family member, for ubiquitination and proteasomal degradation; this alleviates MCL-1 repression of Bak and allows Bak to drive pore formation in the mitochondrial outer membrane (FIG. 5A). Pore formation induces the release of Cyt c into the cytosol and initiates the caspase cascade. A recent publication shows that upregulation of CUL4B leads to increased degradation of HUWE1 and subsequent stabilization of MCL-1, which inhibits Bak by forming a heterodimer and ultimately steers the cell away from apoptosis (Yi et al., 2015).

The inventors captured regulation of this pathway in a time-resolved manner. The CUL4B C-terminal peptide increased at 1 h with a concomitant significant change in HUWE1 phosphorylation. At 6 h post-exposure CUL4B was unchanged, but the inventors observed evidence for a decrease in HUWE1 phosphorylated and unphosphorylated states. Analysis at 24 and 48 h revealed multiple significant abundance changes for phosphorylated peptides of HUWE1 in treated cells, indicating a dynamic regulation process. Additionally, HUWE1 decreased in abundance at 48 h, suggesting that a population of cells were resistant. Although the inventors did not observe MCL-1 at any time point, BAK1 increased at 24 h suggesting that a population of cells were committed to apoptosis. The temporal nature of this pathway highlights the dynamic processes at play in the cisplatin-exposed population, with an apparent early upregulation of pro-survival mechanisms, a later commitment to apoptosis, and detection of an emerging resistant population at 48 h.

Given the dynamic nature of the HUWE1 regulatory circuit, the inventors explored apoptosis and viability pathways using IPA and compared these findings to the empirically derived kinetics of caspase activation and viability. At each time point, IPA sorted significantly changed species in the dataset into apoptosis-inhibiting or -activating categories based on their upregulation or downregulation and correlation with known functions (FIGS. 13A-D). The total number of apoptotic proteins increased up to 24 h and declined by 48 h (FIG. 13A). However, the ratio of activating to inhibiting molecules remained stable at each time point (52-54%), revealing that not all molecular changes are pro-apoptotic (FIG. 13B). The inventors observed similar results when IPA sorted species into viability-inhibiting or -activating categories. The total number of proteins in the viability pathway increased up to 24 h and declined by 48 h, but the ratio of anti- to pro-survival species remained constant (52-57%; FIGS. 13C-D). These trends suggest a heterogeneous population of cells engaged in the dynamic processes of committing to apoptosis or survival.

Consistent with IPA analysis, the measured cellular responses revealed maximal caspase activation at 24 h (FIG. 5B). Both IPA analysis and measured cellular data indicate that caspase activation ceased after 48 h. Indeed, the viability data in FIG. 5B show a small population of cells (c., 20%) persisted to 96 h, suggesting that these cells represent a cisplatin-resistant population. This prompted the inventors to determine if their platform had captured known and novel resistance mechanisms. Such a capability would provide an early indication of drug resistance mechanisms and/or off-target effects—critical knowledge that could improve clinical trial outcomes.

Construction of Cisplatin Resistance Mechanisms.

To validate their capture of resistance mechanisms, the inventors seeded an expanded resistance network (ERN) using the same approach as for the ECN. They identified six proteins in KEGG known to play a role in cisplatin resistance (data not shown). Their expansion resulted in the 1,236-species ERN. The inventors' empirical data contained 667 (54%) of these, 589 of which changed significantly (data not shown). Thus, 88% of the empirically detected species in the ERN changed significantly (FIG. 11). FIG. 5C shows the ERN overlaid on the DDN. The significant overlap of matching nodes validates the presence of known resistance pathways in the inventors' dataset, consistent with a putatively resistant population at 96 h. Thus, the inventors utilized the ERN to generate testable molecular hypotheses for previously reported resistance proteins.

ATP1A1 Mediated Resistance.

ATP1A1, a seed for the ERN and a significantly changed species within the inventors' empirical dataset, regulates cisplatin uptake into cells and modulates resistance when its expression is suppressed (O'Grady et al., 2014). Interestingly, ATP1A1 also regulates activity of Ncx1 (Swift et al., 2008). Abrogation of ATP1A1 function concomitantly attenuates Ncx1 activity, which perturbs the calcium signaling pathways of the cell, a phenomenon associated with evasion of apoptosis and implicated in cancer (Herchuelz et al., 2013; Hong et al., 2015; Markova et al., 2014; Munoz et al., 2015). FIG. 5D shows the ATP1A1 and Ncx1 pathway. ATP1A1 peptides decreased significantly at 6 and 24 h, consistent with enhanced resistance over time. Ncx1 antisense RNA increased at 1 h, with a significant decrease in the Ncx1 transcript measured at 6 h. At 24 h, both the Ncx1 antisense RNA and the Ncx1 transcript decreased. Reduction of Ncx1 expression and function at these early time points may provide escape avenues by perturbing downstream calcium signaling pathways and disrupting the apoptotic circuit. Recently, disruption of intracellular calcium signaling, tolerance of ER stress, and reduced expression of a subunit of calcium-regulated big potassium channels were implicated in cisplatin resistance (Samuel et al., 2016; Xu et al., 2015). Therefore, a better understanding of the pathways that disrupt calcium homeostasis and calcium-regulated apoptotic events is critical to further elucidate cisplatin resistance. Data derived from the inventors' multi-omics dataset for ATP1A1 and Ncx1 present a potential mechanism.

Estrogen-induced cisplatin resistance. Recently, estrogen was shown to mediate resistance to cisplatin-induced apoptosis in A549 cells (Grott et al., 2013). While this study highlighted the importance of caspase attenuation in the mechanism, it did not elucidate a detailed molecular process. The estrogen hormones estrone ($E_1$) and estradiol ($E_2$) are synthesized from androgens by aromatase and can also be interconverted by HSD17βs (Thomas et al., 2013). Additionally, estrogen receptors ESR1 and ESR2 cooperate in promoting early activation of ERK (Chimento et al., 2012). Examination of the estrogen-related pathways in the inventors' dataset revealed a transient metabolomic response to cisplatin-induced cyotoxic stress that ultimately leads to a protein-based resistance mechanism. FIG. 5E demonstrates a network of events derived de novo from measured molecular changes that potentially lead to resistance through mTOR activation. In cisplatin-treated cells, estrogen species transiently increased: $E_1$ increased at 1 h, and both $E_1$ and $E_2$ increased at 6 h but decreased by 24 h. HSD17β7 increased at 1 h and decreased at 6 h. The transcription factor C/EBPβ, which is activated by cyclic AMP (cAMP)-dependent protein kinase A (PKA) (Wilson et al., 2001), regulates HSD17β dehydrogenase family members (Rotinen et al., 2011). At 24 h, the inventors observed an increase in PKA and in HSD17β7 transcript. $E_2$ binds to ESR1 and induces PKC-mediated ERK phosphorylation and ERK-dependent mTOR activation (Panchanthan et al., 2010; Wang et al., 2015). The inventors observed ERK phosphorylation at every time point, with mTOR phosphorylation increased at 24 h.

FIG. 5E also shows the interaction of STAT1 with ESR leading to mTOR activation. STAT1 overexpression mediates cisplatin resistance in ovarian cancer cell lines through an as yet unexplained mechanism (Roberts et al., 2005). Activated STAT1 induces the expression of ESR1, feeding into the above described PKC-ERK mediated activation of mTOR and leading to resistance. Taken together, these data suggest that the STAT1 and estrogen-mediated cisplatin resistance pathways are complementary and that the key elements of the estrogen signaling pathway are activated by 24 h, which may allow escape from cisplatin-induced cytotoxicity by a unique ERK/mTOR axis.

Mining Novel Mechanisms of Cisplatin Resistance.

While the ERN guided identification of associated resistance molecules, pathways outside of the ERN provide the opportunity to discover resistance mechanisms de novo. To explore this, the inventors analyzed the top 20 most dynamically regulated proteins at each time point for potential contribution to mechanisms of resistance and sorted the data based on known links to proliferative capacity or apoptosis.

The STIP1 Cascade.

FIG. 5F illustrates a network of events culminating in potential apoptotic escape mechanisms derived de novo from analysis of measured events in the multi-omics dataset. Based on a dynamic change at 1 h, the inventors identified stress inducible protein 1 (STIP1) as a putative resistance marker. The DDN associates STIP1 with the prion protein PRNP (Baindur-Hudson et al., 2015), which links to the apoptotic activator Bax. Additionally, STIP1 and PRNP associate with cAMP, and activation of the ERK1/2 pathway requires PRNP and STIP1 endocytosis (Erlich et al., 2007). STIP1 binds to PRNP to drive cell proliferation via activation of the MEK/ERK and PI3K pathways. Collectively, this implicates the PI3K, ERK1/2, and cAMP transduction pathways as downstream modulators of the STIP1-PRNP interaction.

Unification of the synergistic activities of PI3K, ERK1/2, and PKA culminating in BAD phosphorylation presents a novel mechanism elucidated de novo from the inventors' empirical data. The right side of FIG. 5F illustrates the ERK-mediated signaling events. As previously discussed, increased levels of activated ERK 1/2 were detected at every time point and likely contribute to apoptosis. However, activated ERK can also contribute to anti-apoptotic pathways via phosphorylation of BAD, emphasizing its pleiotropic effects. The left side of FIG. 5F shows PKA-mediated signaling events. Transcription of catalytic subunits of PKA changed dynamically, with PRKACA upregulated and PRKACB downregulated at 24 h. Functionally, PKA is anchored by binding the AKAP family of proteins, and in the inventors' dataset AKAP13 levels as well as phosphorylation states were dynamically regulated at every time point with overall levels up significantly by 48 h. The center of FIG. 5F displays PI3K-mediated signaling events.

Within this pathway, the inventors detected a number of significant changes at 24-48 h consistent with proliferation in a population of cells. The downstream targets of these pathways, mTOR and BAD, also changed significantly at later time points. Phosphorylated mTOR at pS1166 increased at 24 h. This phosphorylation event was previously identified in response to the pro-proliferative IGF stimulus (Patel et al., 2015), consistent with a role in anti-apoptotic signaling. Additionally, the inventors detected increased BAD phosphorylation at residues that prevent its binding to Bcl-xL/Bcl-2 (Banal et al., 2012; Hayakawa et al., 200): pSer75 (mediated by ERK1/2) at 48 h and pSer118 (mediated by PKA) at 24 h and at 48 h.

Further analysis of the species in these pathways provides insight into cancer development and drug resistance. Overexpression of PRNP in colorectal cancer cells enhances proliferation and attenuates doxorubicin-induced apoptosis (Chieng et al., 2015). Additionally, PRNP upregulates the transcriptional activity of β-catenin/TCF4, which inhibits apoptosis upon cisplatin exposure (Besnier et al., 2015; Liu et al., 2009). Increased levels of cAMP also confer protection against cisplatin-induced DNA damage and apoptosis, likely through PKA activity (von Knethen et al., 1998). STIP1 is a biomarker for many carcinomas, and it is most commonly associated with ovarian cancers. Cell surface interaction of STIP1 and PRNP was first identified as a neuroprotective event that rescued neurons from apoptosis (Zanata et al., 2002). Subsequently, it was determined that neuroprotection is mediated by increasing protein synthesis via the PI3K/mTOR signaling axis (Caetano et al., 2008).

In summary, PI3K, ERK1/2, and cAMP via PKA converge on pro-apoptotic BAD and modulate its phosphorylation. Phosphorylated BAD does not bind and displace Bcl-xL or Bcl-2 from Bak/Bax, preventing Bak/Bax-mediated apoptosis. PI3K and PKA also stimulate mTOR, resulting in stabilization of MCL-1 and further inhibition of the apoptotic pathway by sequestration of Bak (De Joussineau et al., 2014; Koo et al., 2015). As a whole, the STIP1 cascade presented in FIG. 5F ultimately targets mTOR and BAD, disrupting both Bak and Bax and protecting the cell from apoptosis through inhibition of pore formation in the mitochondrial outer membrane.

Critical Insight.

Figure 6:
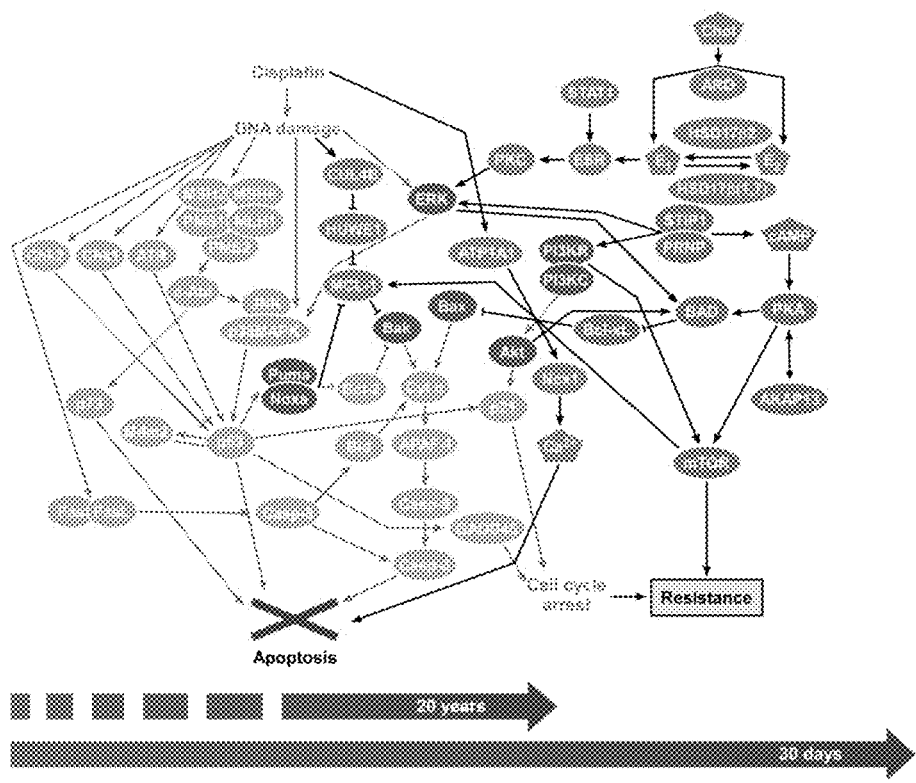
FIG. 6. Integrated molecular response to cisplatin perturbation. The cisplatin canonical MOA (green) determined by multiple groups over a 20 year span integrates with the empirically elucidated pathways: CUL4B/HUWE1 pathway (pink) ATP1A1 pathway (orange); STIP1 cascade (purple); estrogen resistance pathway (teal). Graying represents pathways only from canonical. The comprehensive mechanism obtained in less than 30 days captures possible resistance.
Figure 7:
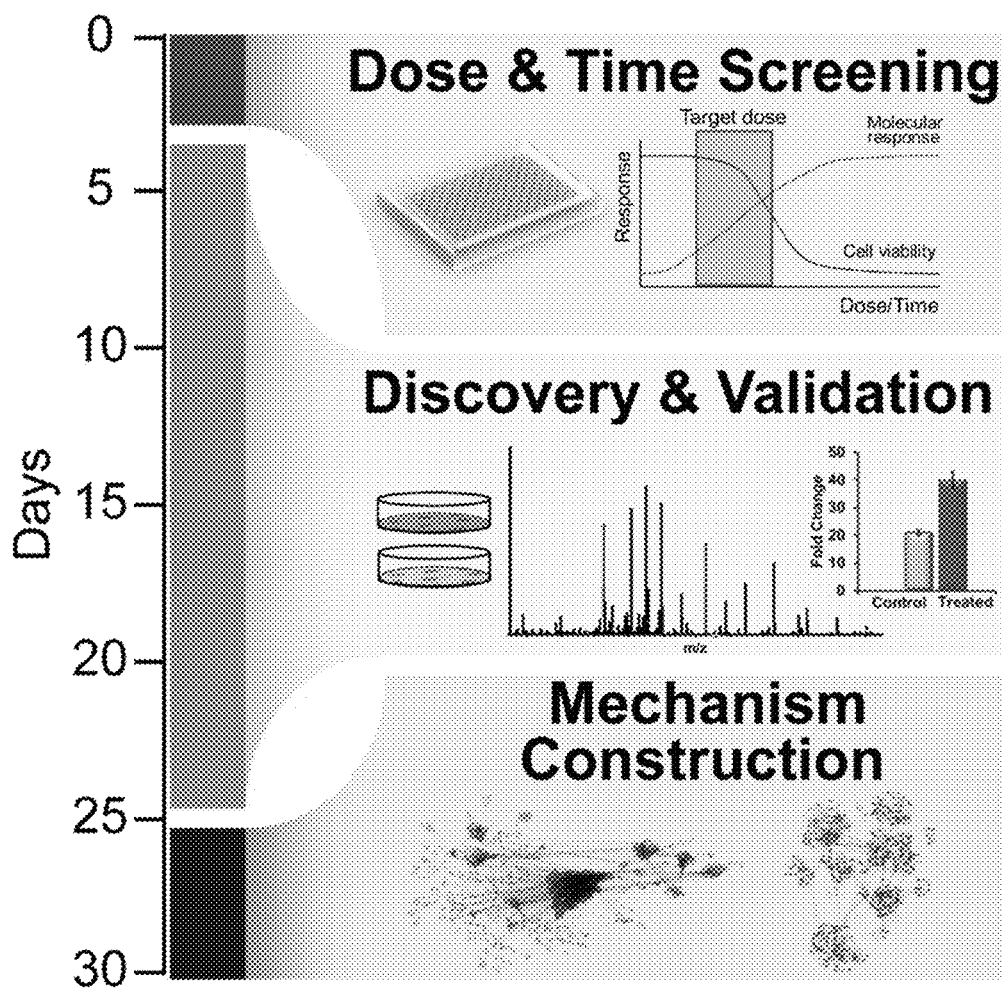
FIG. 7. Graphical abstract of process overview.

The pathways identified de novo by the inventors' 30-day platform integrate with the canonical cisplatin-induced apoptotic pathway generated from decades of research (FIG. 6), suggesting these findings generate valuable testable hypotheses. These analyses highlight only a few pathways represented in the dataset, and further analysis may yield additional hypotheses. This integrated molecular view exemplifies the power of this 30-day multi-omics systems biology approach to global MOA analysis for exogenous compounds.

By using network analysis, this platform captures pathways without directly measuring all pathway members. For example, while MCL-1 was not detected, the MCL-1 pathway was identified as important in apoptosis. The MCL-1 pathway is clinically relevant in resistance to Navitoclax, an experimental Bcl2-family inhibitor that does not target MCL-1. Known mechanisms of resistance to Navitoclax directly depend on MCL-1 levels in cells (Konopleva et al., 2006. The current study suggests that systems level analysis of chemotherapeutics has the potential to identify resistance mechanisms and novel pathways controlling apoptosis.

Example 3

Discussion

The platform described herein utilizes multi-omics technologies for large-scale measurement of molecular events to generate a comprehensive picture of the cellular response to an exogenous compound. Using cisplatin, the inventors demonstrate that this platform can identify primary MOA and pathways important for side effects and resistance. This platform provides several key developments in MOA determination. First, a 3-day screening platform determines relevant exposure and dose, using MS to determine the maximal molecular changes. Second, comprehensive molecular data are collected within 2-3 weeks, including PTMs and metabolomics. These data can generate a tunable output of the final network or mechanism based on statistical confidence in empirical measurements. Last, this platform provides high-throughput, comprehensive MOA assessment. Previous studies successfully identified compound MOA from published datasets of transcriptional changes in response to compounds (Di Bernardo et al., 2005; Woo et al., 2015). This platform collects post-transcriptional and post-translational data to capture MOA beyond gene regulation.

This technology platform determined the cisplatin MOA beyond previous understanding and annotated interactions, and it provides a framework to harness future technological advancements for MOA analysis. Yet, opportunities exist to enhance these capabilities. Parallel analysis of multiple cell lines will allow MOA determination for various tissue or cell types and provide potential for personalized medicine. Addition of sub-cellular fractionation and imaging approaches will facilitate detection of mechanistically important translocation events (e.g., Bax, Cyt c). Integration of functional/causal information with the omics data will also provide great value to MOA analysis. Lastly, expansion of database annotation and the tools for data analysis will advance exploration of these multi-omic datasets. As technology advances, this strategy will incorporate these enhancements, and further improvements will facilitate data acquisition over hundreds of time points, allowing increased resolution of the empirical MOA and permitting statistical tests of causality.

Apart from these enhancements, the inventors' analysis of cisplatin demonstrates that data acquired with this platform provide nearly complete confirmation of the primary MOA for cisplatin cytotoxicity. Furthermore, the data contribute to a more complete description of the biological processes potentially involved in cisplatin resistance. Although these findings require further validation, the results underscore how an integrated omics approach drives the generation of testable hypotheses that directly relate to global cellular responses.

The applications for this platform are diverse and span various fields of study. Assessment of pharmaceutical compounds can rapidly uncover MOA and potential off-target effects as well as improve the selection of drug candidates likely to succeed. This platform could promote rapid MOA assessment for unknown compounds, environmental pollutants, and infectious agents. Additionally, this approach is relevant to the investigation of MOA leading to disease mechanism and developmental abnormalities. While the inventors' present study was performed on monolayer monocultures, it is applicable to suspension cells, as well as three-dimensional tissue constructs and organs-on-chips (Wikswo, 2014). With this range of applications, this platform is an important resource for characterizing global profiles of the biological processes resulting from cellular perturbations.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,313,734
U.S. Pat. No. 4,366,241
U.S. Pat. No. 4,632,901
U.S. Pat. No. 4,683,195
U.S. Pat. No. 4,683,202
U.S. Pat. No. 4,770,853
U.S. Pat. No. 4,786,589
U.S. Pat. No. 4,800,159
U.S. Pat. No. 4,883,750
U.S. Pat. No. 5,242,974
U.S. Pat. No. 5,279,721
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,472,672
U.S. Pat. No. 5,527,681
U.S. Pat. No. 5,529,756
U.S. Pat. No. 5,532,128
U.S. Pat. No. 5,545,531
U.S. Pat. No. 5,554,501
U.S. Pat. No. 5,556,752
U.S. Pat. No. 5,561,071
U.S. Pat. No. 5,571,639
U.S. Pat. No. 5,593,839
U.S. Pat. No. 5,599,695
U.S. Pat. No. 5,624,711
U.S. Pat. No. 5,656,448
U.S. Pat. No. 5,658,734
U.S. Pat. No. 5,700,637
U.S. Pat. No. 5,757,994
U.S. Pat. No. 5,788,166
U.S. Pat. No. 5,838,002
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,986,258
U.S. Pat. No. 6,004,755
U.S. Pat. No. 6,485,982
U.S. Patent RE 35,413
Abbondanzo, *Ann Diagn Pathol*, 3(5):318-327, 1999.
Allred et al., *Arch Surg*, 125(1):107-13, 1990.

Antibodies: A Laboratory Manual, Cold Spring Harbor Laboratory, Cold Spring Harbor Press, Cold Spring Harbor, N.Y., 1988.
Ahuja, V., and Sharma, S. (2014). *J Appl Toxicol* 34, 576-594.
Bahr et al., *J. Mass Spectrom.*, 32:1111-1116, 1997.
Bansal et al., *J. Gynecol. Oncol.* 2012, 23 (1), 35-42.
Baindur-Hudson et al., *Subcell. Biochem.* 2015, 78, 69-90.
Bentzley et al., *Anal Chem.*, 68(13):2141-2146, 1996.
Besnier et al., *Mol. Biol. Cell* 2015, 26 (18), 3313-3328.
Brown et al., *Immunol Ser,* 53:69-82, 1990.
Bucknall et al., *J. Am. Soc. Mass Spectrom.*, 13(9):1015-1027, 2002.
Caprioli et al., *Anal. Chem.*, 69:4751, 1997.
Caetano et al., *J. Neurosci.* 2008, 28 (26), 6691-6702.
Chaurand et al., *Anal Chem.*, 71(23):5263-5270, 1999.
Chen et al., *Nat. Biotechnol.*, 19:537-542, 2001.
Cheng et al., *Biochem. Biophys. Res. Commun.* 2008, 376 (3), 483-488.
Chieng et al., *Tumour Biol.* 2015, 36 (10), 8107-8120.
Chimento et al., *Mol. Cell. Endocrinol.* 2012, 355 (1), 49-59.
Cokelaer et al., *Bioinforma. Oxf. Engl.* 2013, 29 (24), 3241-3242.
Crawford, M. (2010). *State of the Industry 2010.* In *News Magazine* (AAPS), pp. 34-39.
De Jager et al., *Semin Nucl Med* 23(2):165-179, 1993.
De Joussineau et al., *Hum. Mol. Genet.* 2014, 23 (20), 5418-5428.
Desiderio et al., *J. Mass Spectrom.*, 35(6):725-733, 2000.
Desiderio et al., *Methods Mol. Biol.*, 61:57-65, 1996.
Di Bernardo et al., *Nat. Biotechnol.* 2005, 23 (3), 377-383.
DiMasi et al., *Clin Pharmacol Ther* 87, 272-277.
Doolittle et al., *Methods Mol Biol.*, 109:215-237, 1999.
Duncan et al., *Rapid Commun. Mass Spectrom.*, 7(12):1090-1094, 1993.
Engelberg, A. (2004). *Pharmacogenomics* 5, 741-744.
Erlich et al., *Glia* 2007, 55 (16), 1690-1698.
European Appn. 0 125 118
European Appn. 0 143 574
European Appn. 0 282 192
European Appn. 0 299 428
European Appn. 0 364 255
European Appn. 320 308
European Appn. 329 822
Faulstich et al., *Anal. Chem.*, 69(21):4349-4353, 1997.
Fenn et al., *Science*, 246(4926):64-71, 1989.
Frohman, In: *PCR Protocols: A Guide To Methods And Applications*, Academic Press, N.Y., 1990.
Gobom et al., *Anal. Chem.*, 72(14):3320-3326, 2000.
Grott et al., *Anticancer Res.* 2013, 33 (3), 791-800.
Gulbis and Galand, *Hum Pathol* 24(12):1271-1285, 1993.
Hay et al., *Nat Biotechnol* 32, 40-51.
Hayakawa et al., *Cancer Res.* 2000, 60 (21), 5988-5994.
Herchuelz et al., *Adv. Exp. Med. Biol.* 2013, 961, 385-394.
Hong et al., *Biochem. Biophys. Res. Commun.* 2015, 460 (4), 931-937.
Horak et al., *Rapid Commun. Mass Spectrom.*, 15(4):241-248, 2001.
Innis et al., *Proc. Natl. Acad. Sci. USA,* 85(24):9436-9440, 1988.
International Human Genome Sequencing, C. (2004). *Nature* 431, 931-945.
Jensen, O. N. (2004). *Curr Opin Chem Biol* 8, 33-41.
Jespersen et al., *Anal Chem.*, 71(3):660-666, 1999.
Jiang et al., *J. Agric. Food Chem.*, 48:3305, 2000.
Kabarle et al., *Anal. Chem.* 65(20):972A-986A, 1993.
Kalgutkar et al., (2005). *Curr Drug Metab* 6, 161-225.
Kalgutkar, A. S., and Soglia, J. R. (2005). *Expert Opin Drug Metab Toxicol* 1, 91-142.
Kanazawa et al., *Biol. Pharm. Bull.*, 22(4):339-346, 1999.
Kanehisa et al., *Nucleic Acids Res.* 2012, 40 (Database issue), D109-114.
Kazmaier et al., *Anesthesiology,* 89(4):831-817, 1998.
Kola, I., and Landis, J. (2004). *Nat Rev Drug Discov* 3, 711-715.
Konopleva et al., *Cancer Cell* 2006, 10 (5), 375-388.
Koo et al., *Mol. Cell. Biol.* 2015, 35 (13), 2344-2355.
Krejsa et al., (2003). *Curr Opin Drug Discov Devel* 6, 470-480.
Kwoh et al., *Proc. Nat. Acad. Sci. USA,* 86: 1173, 1989.
Li et al., *Trends Biotechnol.*, 18:151, 2000.
Liu et al., *Mol. Carcinog.* 2009, 48 (3), 212-219.
Lopez et al., *CMol. Syst. Biol.* 2013, 9, 646.
Lovelace et al., *J. Chromatogr.*, 562(1-2):573-584, 1991.
Lynn et al., *J. Mol. Evol.*, 48(5):605-614, 1999.
Marie et al., *Anal. Chem.*, 72(20):5106-5114, 2000.
Markova et al., *Pflüg. Arch. Eur. J. Physiol.* 2014, 466 (7), 1329-1342.
Miketova et al., *Mol. Biotechnol.*, 8(3):249-253, 1997.
Milne et al., *Biochemistry* 52, 3829-3840.
Mirgorodskaya et al., *Rapid Commun. Mass Spectrom.*, 14(14):1226-1232, 2000.
Muddiman et al., *Fres. J. Anal. Chem.*, 354:103, 1996.
Mueller and Wold, *Science* 246, 780-786, 1989.
Muñoz et al., *J. Urol.* 2015, 194 (1), 245-251.
Nakamura et al., In: *Handbook of Experimental Immunology* (4$^{th}$ Ed.), Weir et al., (eds). 1:27, Blackwell Scientific Publ., Oxford, 1987.
Nelson et al., *Anal. Chem.*, 66:1408, 1994.
Nguyen et al., *J. Chromatogr. A.*, 705(1):21-45, 1995.
O'Grady et al., *Cancer Treat. Rev.* 2014, 40 (10), 1161-1170.
Ohara et al., *Proc. Nat'l Acad. Sci. USA,* 86: 5673-5677, 1989.
Ou et al., *Mol Biol Cell* 2005, 16 (4), 1684-1695.
Panchanathan et al., *PloS One* 2010, 5 (5), e10868.
Patel et al., Quantitative analysis of AKT/mTOR pathway using immunoprecipitation and targeted mass spectrometry, 2015.
PCT Appln. WO 88/10315
PCT Appln. WO 89/06700
PCT Appln. WO 88/08534
PCT Appln. WO 90/07641
PCT Appln. PCT/US89/01025
PCT Appln. PCT/US87/00880
Roberts et al., *Br. J. Cancer* 2005, 92 (6), 1149-1158.
Roepstorff, *EXS.*, 88:81-97, 2000.
Rotinen et al., *Mol. Cell. Endocrinol.* 2011, 339 (1-2), 45-53.
Sakaguchi et al., *Biochemistry (Mosc.)* 1997, 36 (33), 10117-10124.
Sambrook et al., In: *Molecular Cloning: A Laboratory Manual,* 2nd Ed., Cold Spring Harbor Press, Cold Spring Harbor, N.Y., 1989.
Samuel et al., *Tumour Biol.* 2016, 37 (2), 2565-2573.
Sasseville et al., (2004). *Chem Biol Interact* 150, 9-25.
Sereni et al., *Methods in Molecular Biology* 986, 187-214.
Shannon et al., *Genome Res.* 2003, 13 (11), 2498-2504.
Slee et al., *J. Cell Biol.* 1999, 144 (2), 281-292.
Stoeckli et al., *Nat. Med.*, 7(4):493-496, 2001.
Swift et al., *Cardiovasc. Res.* 2008, 78 (1), 71-78.
Takach et al., *J. Protein Chem.*, 16:363, 1997.
Taylor et al., *Nat. Rev. Mol. Cell Biol.* 2008, 9 (3), 231-241.
Thomas and Potter, *J. Steroid Biochem. Mol. Biol.* 2013, 137, 27-49.

Tufts Center for the Study of Drug Development (2014). News. In Cost to Develop and Win Marketing Approval for a New Drug Is $26 Billion (Boston, Mass.: Tufts University).
Villanueva et al., *Enzyme Microb. Technol.*, 29:99, 1999.
von Knethen et al., *Oncogene* 1998, 17 (3), 387-394.
Walker et al., *Proc. Natl. Acad. Sci. USA*, 89:392-396 1992.
Walsh, C. (2006). Posttranslational Modification of Proteins: Expanding Nature's Inventory (Roberts and Company Publishers).
Walsh et al., *Angew Chem Int Ed Engl* 44, 7342-7372.
Wang et al., *Anal. Chem.*, 72(21):5285-5289, 2000.
Wang et al., *J. Agric. Food. Chem.*, 47:1549, 1999.
Wang et al., *J. Agric. Food. Chem.*, 47:2009, 1999.
Wang et al., *Proc. Natl. Acad. Sci. U.S.A* 2015, 112 (11), E1382-1391.
Wikswo, J. P., *Exp. Biol. Med.* 2014, 239 (9), 1061-1072.
Wilson et al., *Mol. Cell. Endocrinol.* 2001, 181 (1-2), 27-34.
Wittmann et al., *Biotechnol. Bioeng.*, 72:642, 2001.
Woo et al., *Cell* 2015, 162 (2), 441-451.
Wu et al., *Anal. Chem.*, 70:456A, 1998.
Wu et al., *Biochem. Biophys. Res. Commun.*, 233(1):221-226, 1997.
Wu et al., *Biochim. Biophys. Acta*, 1466:315-327, 2000.
Xu et al., *Oncol. Rep.* 2015, 34 (6), 3051-3060.
Yang et al., *Proc Natl. Acad. Sci. USA*, 87:9568-9572, 1990.
Yang et al., *PloS One* 2013, 8 (5), e65309.
Yi et al., *Nucleic Acids Res.* 2015, 43 (9), 4579-4590.
Zanata et al., *EMBO J.* 2002, 21 (13), 3307-3316.
Zhang et al., *Tumour Biol* 2015.
Zhong et al., *Clin. Chem. ACTA.*, 313:147, 2001.
Zhong et al., *Cell* 2005, 121 (7), 1085-1095.
Zweigenbaum et al., *Anal. Chem.*, 71(13):2294-300, 1999.
Zweigenbaum et al., *J. Pharm. Biomed. Anal.*, 23(4):723-733, 2000.

What is claimed is:

1. A method of identifying a biological mechanism for a drug or toxin comprising:
   (a) providing a known or unknown drug or toxin;
   (b) determining an optimal dosage and exposure time for said drug or toxin on a biological system by
      (i) first determining an optimal dosage and exposure time for said drug or toxin on cell viability; and then
      (ii) determining an optimal dosage and exposure time for said drug or toxin on changes in protein, RNA or metabolite levels in a comparable cell, wherein said optimal dosage and exposure time maximizes the observation of one or more biological parameters of a biological mechanism in said biological system;
   (c) exposing said drug or toxin under said optimal dosage and exposure time to said biological system;
   (d) assessing one or more of said biological parameters in said biological system that is/are altered, as compared to an untreated biological system, thereby identifying one or more biological effects for said drug or toxin; and
   (e) analyzing one or more biological effects of step (d) to identify one or more biological mechanisms for said drug or toxin, wherein said one or more effects comprises changes enzyme activity, protein levels, nucleic acid levels, lipid levels, carbohydrate levels, metabolite levels, protein phosphorylation levels, post translational modification, average protein size, organelle function, tissue integrity or function, organ function, cell morphology, integrity, activity or viability, or organism activity or viability.

2. The method of claim 1, wherein said biological system is a purified enzyme, a purified subcellular organelle, a cell, a tissue, an organ, an organ system or an organism.

3. The method of claim 1 or claim 2, wherein determining an optimal dosage and exposure time comprises exposing said biological system to a plurality of different doses and exposure time and measuring one or more effects of said drug or toxin on said biological system.

4. The method of claim 1, wherein cell viability is determined by microscopy or by a biological marker (e.g., caspase activation or ATP utilization).

5. The method of claim 1, wherein step (d) comprises RPLC, HILIC chromatography, RNA sequencing, mass spectrometry, ion mobility mass spectrometry, genomic analysis, protein array, or immunoassay.

6. The method of claim 1, wherein steps (c) and (d) are performed for multiple time points.

7. The method of claim 1, wherein step (b)(ii) comprises RPLC, HILIC chromatography, RNA sequencing, mass spectrometry, ion mobility mass spectrometry, genomic analysis, protein array, or immunoassay.

8. The method of claim 1, further comprising validating said one or more biological parameters.

9. The method of claim 8, wherein validating comprises mechanistic validation and/or cross-platform validation.

10. The method of claim 1, wherein steps (a) and (b) are performed in 3 days or less.

11. The method of claim 1, wherein steps (a)-(e) are performed in 30 days or less.

* * * * *

UNITED STATES PATENT AND TRADEMARK OFFICE
CERTIFICATE OF CORRECTION

| | | |
|---|---|---|
| PATENT NO. | : 10,607,721 B2 | Page 1 of 1 |
| APPLICATION NO. | : 15/273259 | |
| DATED | : March 31, 2020 | |
| INVENTOR(S) | : Caprioli et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 387 days.

Signed and Sealed this
Twenty-fourth Day of November, 2020

Andrei Iancu
*Director of the United States Patent and Trademark Office*